(12) United States Patent
Nakajou et al.

(10) Patent No.: US 7,943,570 B2
(45) Date of Patent: May 17, 2011

(54) SUGAR CHAIN-CONTAINING ALBUMIN, PRODUCTION METHOD THEREOF AND USE THEREOF

(75) Inventors: Keisuke Nakajou, Osaka (JP); Naohisa Katayama, Osaka (JP); Toshiya Kai, Osaka (JP); Masaki Otagiri, Kumamoto (JP)

(73) Assignee: Nipro Corporation, Osaka-shi (JP)

( * ) Notice: Subject to any disclaimer, the term of this patent is extended or adjusted under 35 U.S.C. 154(b) by 10 days.

(21) Appl. No.: 11/873,393

(22) Filed: Oct. 16, 2007

(65) Prior Publication Data

US 2009/0099071 A1   Apr. 16, 2009

(51) Int. Cl.
*C07K 14/00* (2006.01)
(52) U.S. Cl. .......................................... 514/2; 530/350
(58) Field of Classification Search .................. None
See application file for complete search history.

(56) References Cited

FOREIGN PATENT DOCUMENTS

JP         2008-43285 A     2/2008

OTHER PUBLICATIONS

Taguchi et al. 1999; Inhibition of advanced protein glycation by Schiff base between aminoguanidine and pyridoxyl. Eur. J. Pharm. 378(3): 283-289.*
Candiano et al. 1984; Glycosylation of human albumin in diabetes mellitus: Extensive microheterogeneity of serum and urinary species as revealed by isoelectric focusing. Electrophoresis 5: 217-222.*
Yang et al. 1994; Advanced glycation end products up-regulate gene expression found in diabetic glomerular disease. PNAS 91(20): 9436-9440.*
www.macromolecularinsights/albumin.php (2009).*
Makita et al. 1992; Immunodetection of advanced glycosylation end-products in vivo. Journal Biol. Chem. 267: 5133-5138.*
Bause 1983; Structural requirements of N-glycosylation of proteins. Biochem J. 209:331-336.*
Higuchi et al., *International Journal of Pharmaceutics*, 287: 147-154 (2004).
Lee et al., *Biochemistry*, 15(18): 3956-3963 (Sep. 7, 1976) (Abstract).
Nishikawa et al., *Am. J. Physiol. Gastrointest. Liver Physiol*, 268: G849-G856 (1995).
Opanasopit et al., *Am. J. Physiol. Gastrointest. Liver Physiol.*, 280: 879-889 (2001).
Takakura et al., *Biochemical Pharmacology*, 47(5): 853-858 (1994).
Yamasaki et al., *The Journal of Pharmacology and Experimental Therapeutics*, 301(2): 467-477 (2002).
Brennan et al., *Proc. Natl. Acad. Sci. USA*, 87: 26-30 (Jan. 1990).
Melgert et al., *Hepatology*, 34(4): 719-728 (2001).
Peach et al., *Biochimica et Biophysica Acta.*, 1097: 49-54 (1991).
Sakamoto et al. *Biochim. Biophys. Acta*, 1252: 209-216 (1995).
Meyers, Robert A., ed., "Glycoproteins, Secretory" in *Molecular Biology and Biotechnology: A Comprehensive Desk Reference* (VCH Publishers, Inc., New York, 1995), p. 390.

* cited by examiner

*Primary Examiner* — Karen Cochrane Carlson
(74) *Attorney, Agent, or Firm* — Leydig, Voit & Mayer, Ltd.

(57) ABSTRACT

Glycosylated albumin as a drug carrier for a DDS targeting the liver (particularly kupffer's cell) can be provided by mutating a DNA encoding albumin to encode a mutant albumin containing a partial amino acid sequence permitting glycosylation modification by eukaryotic cell, preferably a consensus sequence of N-linked sugar chain, introducing an expression vector containing the mutant DNA into a host eukaryotic cell, preferably a host cell permitting addition of a high-mannose type sugar chain, culturing the obtained transformant, and recovering a glycosylated albumin protein from the obtained culture.

12 Claims, 2 Drawing Sheets

SUGAR CHAIN-CONTAINING ALBUMIN, PRODUCTION METHOD THEREOF AND USE THEREOF

INCORPORATION-BY-REFERENCE OF MATERIAL ELECTRONICALLY SUBMITTED

Incorporated by reference in its entirety herein is a computer-readable nucleotide/amino acid sequence listing submitted concurrently herewith and identified as follows: 30,551 bytes ASCII (Text) file named "702141SequenceListing.txt," created Dec. 26, 2007.

TECHNICAL FIELD OF THE INVENTION

The present invention relates to a novel glycosylated albumin protein, wherein a sugar chain is selectively added to a particular amino acid residue, a production method thereof and use thereof. More particularly, the present invention relates to a glycosylated albumin protein wherein a sugar chain is selectively added to a partial amino acid sequence contained in a mutant albumin, which partial amino acid sequence is possibly subject to a glycosylation modification by a host cell, a DNA encoding the mutant albumin, a production method of the glycosylated albumin protein, comprising cultivating eukaryotic cell containing the DNA, and use of the protein as a drug carrier.

BACKGROUND OF THE INVENTION

Human serum albumin (hereinafter sometimes to be referred to as "HSA") is widely distributed in the body, including blood and intercellular fluids. Its primary structure consists of 585 amino acids, and it is a simple protein having a molecular weight of about 66.5 kDa, which is free of a sugar structure. This protein is produced in the liver, mainly maintains normal osmotic pressure in the bloodstream, and is responsible for maintaining the liquid content of the blood. Therefore, HSA is used in various clinical situations for the treatment of a condition associated with loss of liquid from the blood vessel, such as surgery, shock, burn, hypoproteinemia causing edema and the like.

In addition, HSA functions as a carrier of various serum molecules, and is rich in safety, biocompatibility, biodegradation property, persistence in blood and the like. Therefore, it is considered a preferable carrier for a drug delivery system (DDS) of a drug having a problem in the kinetic property.

The DDS based on an irreversible bond between HSA and a drug includes a method improving persistence in blood of the drug bonded utilizing the long half-life of HSA, and a method using a modified form of HSA as a carrier of the active transport system. In the former, an attempt has been made to express a protein or a bioactive peptide having a short half-life as a hybrid by a gene fusion technique. In the latter, a method of controlling the physicochemical properties of HSA such as anionization and cationization, and an attempt to realize accurate kinetic control and cell-specific targeting by introduction of a recognition element (apparatus) of a receptor, which is present on the cell surface, such as sugar structure and peptide have been intensively studied (Lee Y C et al., Biochemistry, 15: 3956-3963, 1976, Opanasopit P et al., Am. J. Physiol. Gastrointest. Liver Physiol. 280: 879-889, 2001, Takakura Y et al., *Biochemical Pharmacology* 47: 853-858, 1994, Yamasaki Y et al., J. Pharmacol. Exp. Then 301: 467-477, 2002. Nishikawa M et al., Am. J. Physiol. Gastrointest. Liver Physiol. 268:0849-G856, 1995, Higuchi Y et al., int. J. Pharm. 287: 147-154, 2004).

It is known that a receptor that recognizes sugar residue and negative charge is present in the liver. Using this property, albumin bound with succinic acid, galactose, mannose and the like is used for targeting the liver.

However, for chemical modification of HSA, the following problems have been pointed out.
(1) The liver does not recognize unless very many sugar residues are bound;
Galactose-modified albumin is not recognized by the liver unless 10 or more galactoses are bound per albumin molecule (see Nishikawa M et al., Am. J. Physiol. Gastrointest. Liver Physiol. 268:G849-G856, 1995).
(2) The cell specificity to liver nonparenchymal cell is low;
Mannose- or fucose-modified albumin is known to be introduced into the both cells of liver endothelial cell and kupffer's cell (see Higuchi Y et al., Int. J. Pharm. 287: 147-154, 2004).
(3) A uniform bound form is difficult to prepare, and appropriate binding conditions need to be found; and the like.
Accordingly, there is a strong demand for the development of a method for modifying HSA by a non-chemical technique.

It is an object of the present invention to provide uniform glycosylated albumin, particularly serum albumin, which specifically transfer to the liver, particularly kupffer's cell, thereby providing a drug carrier suitable for DDS to the liver.

The present inventors have conducted intensive studies in an attempt to solve the aforementioned problems and succeeded in preparing a glycosylated HSA with high liver transferability wherein a high-mannose type sugar chain is added to the Asn residue of a consensus sequence (Asn-X-Thr/Ser) by introducing the consensus sequence of an N-linked sugar chain into a DNA encoding HSA by site-directed mutagenesis, and cultivating *Pichia pastoris* transformed with an expression vector containing the obtained DNA encoding a mutant HSA, which resulted in the completion of the present invention.

SUMMARY OF THE INVENTION

Accordingly, the present invention provides the following.
[1] A glycosylated albumin protein comprising a mutant albumin and a sugar chain, wherein the mutant albumin contains one or more partial amino acid sequences possibly subject to a glycosylation modification by an eukaryotic cell, and the sugar chain is selectively added to the partial amino acid sequence(s).
[2] The protein of the above-mentioned [1], wherein the sugar chain is a high-mannose type sugar chain.
[3] The protein of the above-mentioned [1] or [2], wherein at least one of the partial amino acid sequences is Asn-Xaa-Thr or Asn-Xaa-Ser (Xaa is any genetically encoded amino acid).
[4] The protein of the above-mentioned [3], wherein all the partial amino acid sequences are Asn-Xaa-Thr or Asn-Xaa-Ser (Xaa is any genetically encoded amino acid).
[5] The protein of any of the above-mentioned [1] to [4], wherein the albumin is human serum albumin.
[6] The protein of the above-mentioned [5], which has an amino acid sequence the same as or substantially the same as the amino acid sequence shown in amino acid numbers 1-585 in the amino acid sequence shown in SEQ ID NO: 2, wherein the 63rd amino acid is Asn and/or the 320th amino acid is Thr or Ser and/or the 494th amino acid is Asn.
[7] The protein of the above-mentioned [6], wherein at least the 494th amino acid is Asn.
[8] A DNA encoding a mutant albumin containing one or more partial amino acid sequences possibly subject to a glycosylation modification by an eukaryotic cell.

[9] An expression vector comprising the DNA of the above-mentioned [8], which is under regulation of a promoter functional in a host eukaryotic cell.
[10] A transformant obtained by introducing the expression vector of the above-mentioned [9] into a host eukaryotic cell.
[11] The transformant of the above-mentioned [10], wherein the host eukaryotic cell is a yeast.
[12] The transformant of the above-mentioned [11], wherein the yeast belongs to the genus *Pichia*.
[13] A method of producing the protein of the above-mentioned [1], which comprises culturing the transformant of any of the above-mentioned [10]-[12] in a medium, and recovering glycosylated albumin from the obtained culture.
[14] A pharmaceutical agent comprising the protein of any of the above-mentioned [1]-[7].
[15] A drug carrier to the liver, which comprises the protein of any of the above-mentioned [1]-[7].
[16] The carrier of the above-mentioned [15], wherein the target cell is a kupffer's cell.
[17] A pharmaceutical composition comprising a pharmaceutical compound to be delivered to the liver, and the carrier of the above-mentioned [15] or [16].

Since the glycosylated albumin of the present invention is specifically introduced into the liver, particularly liver non-parenchymal cell, more particularly kupffer's cell, it can be used as a drug carrier for the cell. For example, when the glycosylated albumin of the present invention is bound with an antioxidant or nitric oxide and administered to hepatic ischemia-reperfusion injury, a superior treatment effect can be expected. Moreover, since the liver clearly recognizes even one sugar chain, the albumin can be used without influencing the original structure and function of albumin. In addition, since the albumin is a gene recombinant protein, it is free of a risk of contamination with an unknown virus and the like, which is a problem specific to blood-derived preparations, and can be used safely for human body and the like.

DETAILED DESCRIPTION OF THE INVENTION

Figure 1:
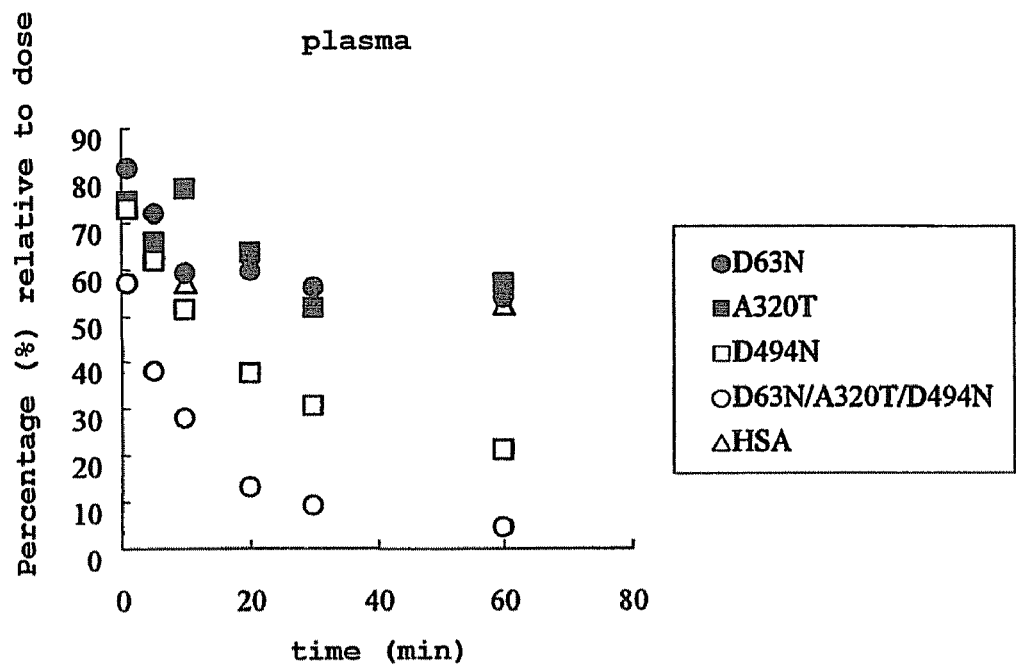
FIG. 1 is a graph showing the time course changes of transferability of glycosylated human serum albumin of the present invention to plasma (upper) and liver (lower) in Experimental Example 1, wherein the vertical axis shows a percentage (%) relative to dose and the transverse axis shows time (min) after administration.
Figure 1:
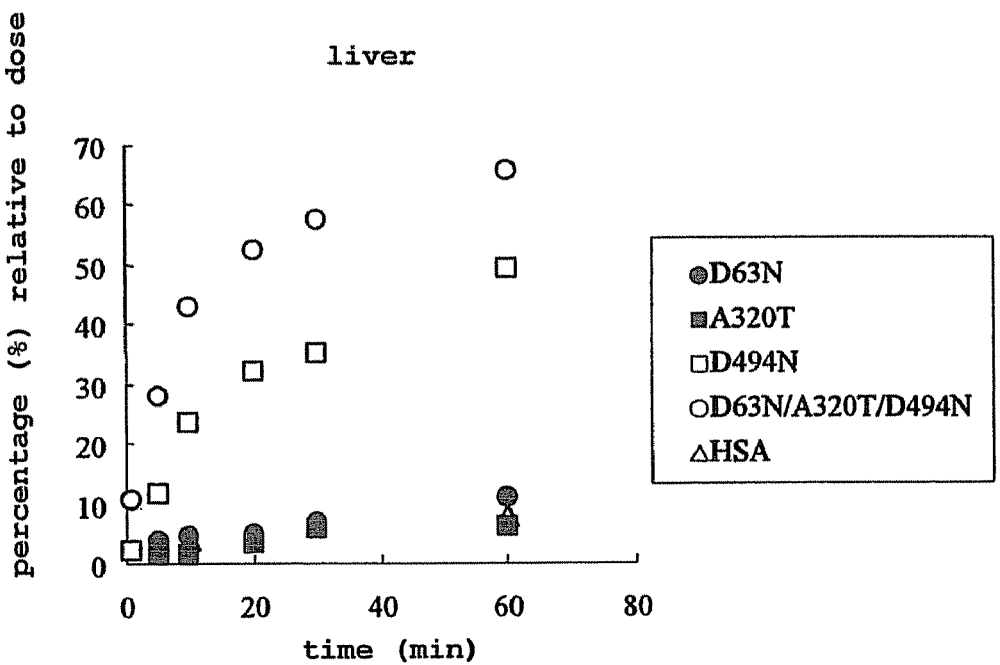

Examples of the albumin in the present invention include serum albumin, egg white albumin and the like, with preference given to serum albumin. While the origin of albumin is not particularly limited, for example, human and other warm-blooded animals (e.g., bovine, monkey, swine, equine, sheep, goat, canine, feline, rabbit, mouse, rat, hamster, guinea pig, chicken, quail etc.) can be mentioned. In consideration of use as a pharmaceutical agent or a carrier of a pharmaceutical compound, preferred is human albumin, more preferred is human serum albumin (HSA). In the following, the present invention is sometimes explained in detail by referring to HSA as an example. Those of ordinary skill in the art can produce and utilize glycosylated albumin in the same manner based on the description in the present specification and other known sequence information of albumin.

The glycosylated albumin of the present invention is a mutant albumin containing one or more partial amino acid sequences possibly subject to a glycosylation modification by an eukaryotic cell, wherein a sugar chain is selectively added to the partial amino acid sequence. Examples of the "partial amino acid sequences possibly subject to a glycosylation modification by an eukaryotic cell" (hereinafter sometimes to be also referred to as "glycosylation sequence") include, but are not limited to, Asn-Xaa-Thr or Asn-Xaa-Ser (Xaa is amino acid genetically coded for and a sugar chain is added to Asn residue) (hereinafter comprehensively abbreviated as "Asn-Xaa-Thr/Ser"), which are consensus sequences of an N-linked sugar chain, Cys-Xaa-Xaa-Gly-Gly-Thr/Ser (Xaa is as defined above, and a sugar chain is added to Thr/Ser residue), which is a consensus sequence of O-linked fucose from among O-linked sugar chains, Cys-Xaa-Ser-Xaa-Pro-Cys (Xaa is as defined above, and a sugar chain is added to Ser residue), which is a consensus sequence of O-linked glucose and the like. Preferred is Asn-Xaa-Thr/Ser, which is a consensus sequence of N-linked sugar chain. The number of the glycosylation sequences may be one or more. While the liver, particularly kupffer's cell, targeting efficiency is improved as the number of sugar chains increases, in consideration of the maintenance of the original physiological function of albumin and the antigenicity problem, a smaller number of sugar chains to be added is more advantageous. As mentioned below, the liver targeting function does not simply depend on the number of sugar chains to be added, but varies depending on the site of addition. Thus, introduction of a glycosylation sequence into a site highly contributing to the targeting efficiency achieves superior targeting efficiency with a small number of sugar chains.

Since natural (wild-type) albumin is a simple protein, it does not have a partial amino acid sequence that may undergo a glycosylation modification by an eukaryotic cell. Accordingly, the glycosylated albumin of the present invention comprises a mutant amino acid sequence containing the above-mentioned glycosylation sequence. While the mutant albumin polypeptide of the present invention may be obtained by any method, for a sugar chain to be selectively added to the glycosylation sequence in the polypeptide, the mutant albumin polypeptide is preferably provided by cultivating an eukaryotic cell containing a DNA encoding the same.

While the eukaryotic cell containing a DNA encoding the mutant albumin can also be obtained, for example, by inducing a mutation in artificially or artificially (e.g., treatment with mutagenic agent such as EMS and the like, UV treatment and the like) in a cell (e.g., hepatocyte and the like) inherently producing albumin and screening for a cell producing a mutant albumin containing a glycosylation sequence, it can be more preferably produced by cloning a DNA encoding albumin, introducing a base sequence encoding a glycosylation sequence into the DNA by a genetic manipulation, inserting the obtained mutant DNA into an expression vector containing a promoter functional in a suitable host eukaryotic cell so that it will enter the control of the promoter, and transforming the host eukaryotic cell with the obtained mutant albumin expression vector.

Examples of the DNA encoding albumin include genomic DNAs derived from human or other warm-blooded animals, cDNAs derived from albumin-producing cells (e.g., hepatocyte and the like), synthetic DNA and the like. The genomic DNA or cDNA encoding albumin can also be directly amplified by Polymerase Chain Reaction (hereinafter abbreviated as "PCR method") or Reverse Transcriptase-PCR (hereinafter abbreviated as "RT-PCR method") using a genomic DNA fraction or a total RNA or mRNA fraction prepared from the producing cells or tissues (e.g., liver and the like) as a template. Alternatively, the genomic DNA or cDNA encoding albumin can also be cloned by colony or plaque hybridization method, PCR method and the like from a genomic DNA library or cDNA library prepared by inserting a fragment of genomic DNA or total RNA or mRNA prepared from the above-mentioned cell/tissue into a suitable vector. The vector to be used for the library may be any of bacteriophage, plasmid, cosmid, phagemid and the like.

Examples of the DNA encoding albumin include a DNA containing a base sequence encoding an amino acid sequence the same as or substantially the same as the amino acid sequence shown in amino acid numbers 1-585 in the amino acid sequence shown in SEQ ID NO: 4 (wild-type mature HSA) and the like. As the amino acid sequence substantially the same as the amino acid sequence shown in amino acid numbers 1-585 in the amino acid sequence shown in SEQ ID NO: 4, an amino acid sequence having a homology of not less than about 80%, preferably not less than about 90%, more preferably not less than about 95%, particularly preferably not less than about 98% with the amino acid sequence shown in the amino acid sequence shown in amino acid numbers 1-585 in the amino acid sequence shown in SEQ ID NO: 4 and the like can be mentioned. As used herein, by the "homology" is meant the proportion (%) of the same amino acid and similar amino acid residues relative to the total overlapping amino acid residues in the optimal alignment when two amino acid sequences are aligned using a mathematical algorithm known in the art (preferably, the algorithm is capable of considering introduction of a gap into one or both of the sequences for the optimal alignment). The "similar amino acid" means an amino acid similar in the physicochemical properties. For example, amino acids classified in the same group such as aromatic amino acids (Phe, Trp, Tyr), aliphatic amino acids (Ala, Leu, Ile, Val), polar amino acids (Gln, Asn), basic amino acids (Lys, Arg, His), acidic amino acids (Glu, Asp), amino acids (Ser, Thr) having a hydroxyl group, amino acids (Gly, Ala, Ser, Thr, Met) with small side chain and the like can be mentioned. It is predicted that substitution with such similar amino acids will not alter protein phenotypes (namely, preservative amino acid substitution). Specific examples of preservative amino acid substitution are well known in the art and are described in various literatures (see e.g., Bowie et al., Science, 247: 1306-1310 (1990)).

The homology of the amino acid sequence in the present specification can be calculated using homology calculation algorithm NCBI BLAST (National Center for Biotechnology Information Basic Local Alignment Search Tool) under the following conditions (expectancy=10; allowing gap; matrix=BLOSUM62; filtering=OFF). Other algorithms for determining the homology of the amino acid sequence include, for example, the algorithm described in Karlin et al., Proc. Natl. Acad. Sci. USA, 90: 5873-5877 (1993) [this algorithm is incorporated in the NBLAST and XBLAST program (version 2.0) (Altschul et al., Nucleic Acids Res., 25: 3389-3402 (1997))], the algorithm described in Needleman et al., J. Mol. Biol., 48: 444-453 (1970) [this algorithm is incorporated in the GAP program in the GCG software package], the algorithm described in Myers and Miller, CABIOS, 4: 11-17 (1988) [this algorithm is incorporated in the ALIGN program (version 2.0) which is a part of the CGC sequence alignment software package], the algorithm described in Pearson et al., Proc. Natl. Acad. Sci. USA, 85: 2444-2448 (1988) [this algorithm is incorporated in the FASTA program in the GCG software package] and the like, and they can also be used preferably.

More preferably, an amino acid sequence substantially the same as the amino acid sequence shown in amino acid numbers 1-585 in the amino acid sequence shown in SEQ ID NO: 4 has homology of not less than about 80%, preferably not less than about 90%, more preferably not less than about 95%, particularly preferably not less than about 98%, to the amino acid sequence shown in amino acid numbers 1-585 in the amino acid sequence shown in SEQ ID NO: 4.

A protein containing an amino acid sequence substantially the same as the amino acid sequence shown in amino acid numbers 1-585 in the amino acid sequence shown in SEQ ID NO: 4 means a protein containing an amino acid sequence substantially the same as the aforementioned amino acid sequence shown in amino acid numbers 1-585 in the amino acid sequence shown in SEQ ID NO: 4 and having a substantially equivalent activity to that of the protein containing the amino acid sequence shown in amino acid numbers 1-585 in the amino acid sequence shown in SEQ ID NO: 4.

The substantially the equivalent activity includes, for example, physiological function of albumin (particularly serum albumin), such as function as a carrier of serum molecules, function to maintain plasma colloidal osmotic pressure and the like. The "substantially equivalent" means that the functions are qualitatively the same. Therefore, the function as a carrier of the serum molecules and the like is preferably equivalent, but the quantitative elements such as the level of the function, molecular weight of the protein and the like may be different.

In addition, the DNA encoding albumin includes, for example, DNA encoding a protein containing (1) an amino acid sequence wherein one or more (preferably about 1-30, more preferably about 1-10, particularly preferably 1—several (2, 3, 4 or 5)) amino acids are deleted from the amino acid sequence shown in amino acid numbers 1-585 of the amino acid sequence shown in SEQ ID NO: 4, (2) an amino acid sequence wherein one or more (preferably about 1-30, more preferably about 1-10, particularly preferably 1—several (2, 3, 4 or 5)) amino acids are added to the amino acid sequence shown in amino acid numbers 1-585 in the amino acid sequence shown in SEQ ID NO: 4, (3) an amino acid sequence wherein one or more (preferably about 1-30, more preferably about 1-10, particularly preferably 1—several (2, 3, 4 or 5)) amino acids are inserted in the amino acid sequence shown in amino acid numbers 1-585 in the amino acid sequence shown in SEQ ID NO: 4, (4) an amino acid sequence wherein one or more (preferably about 1-30, more preferably about 1-10, particularly preferably 1—several (2, 3, 4 or 5)) amino acids are substituted by other amino acids in the amino acid sequence shown in amino acid numbers 1-585 in the amino acid sequence shown in SEQ ID NO: 4, or (5) a combination of these, and the like.

When the amino acid sequence is inserted, deleted or substituted as mentioned above, the site of the insertion, deletion or substitution is not particularly limited as long as the activity of protein is maintained.

More preferably, a DNA encoding albumin (particularly HSA) includes, for example, a DNA containing the base sequence shown in base numbers 73-1827 in the base sequence shown in SEQ ID NO: 3, a DNA encoding a protein having a base sequence hybridizing to the base sequence shown in SEQ ID NO: 3 under stringent conditions, and having substantially equivalent activity (e.g., function of serum molecule as a carrier and the like) to a protein containing the aforementioned amino acid sequence shown in amino acid numbers 1-585 of the amino acid sequence shown in SEQ ID NO: 4, and the like. As the DNA capable of hybridizing to the base sequence shown in SEQ ID NO: 3 under stringent conditions, for example, a DNA containing a base sequence having, in an overlapping region, a homology of not less than about 80%, preferably not less than about 90%, more preferably not less than about 95%, to the base sequence shown in base numbers 73-1827 in the base sequence shown in SEQ ID NO: 3 and the like can be used.

The homology of the base sequence in the present specification can be calculated using a homology calculation algorithm NCBI BLAST (National Center for Biotechnology Information Basic Local Alignment Search Tool) under the following conditions (expectancy=10; allowing gap; filtering=ON; match score=1; mismatch score=−3). Preferable examples of other algorithms usable for determining homology of the base sequence include the above-mentioned homology calculation algorithms for amino acid sequence.

Hybridization can be performed according to a method known per se or a method according to the method, for example, the method described in Molecular Cloning, ver. 2 (J. Sambrook et al., Cold Spring Harbor Lab. Press, 1989) and the like. When a commercially available library is used, moreover, hybridization can be performed according to the method described in the attached instruction manual. Preferably, hybridization can be performed under high stringent conditions.

The high stringent conditions include, for example, a hybridization reaction at 45° C. in 6×SSC (sodium chloride/sodium citrate), and washing one or more times at 65° C. in 0.2×SSC/0.1% SDS and the like. Those of ordinary skill in the art can easily adjust to the desired stringency by appropriately changing the salt concentration of hybridization solution, temperature of hybridization reaction, probe concentration, length of probe, number of mismatches, hybridization reaction time, salt concentration of washing solution, temperature of washing and the like.

A DNA encoding albumin (particularly HSA) can be cloned by amplifying by PCR method using a synthetic DNA primer having a part of the base sequence encoding albumin, or hybridizing DNA incorporated into a suitable expression vector to with a labeled DNA fragment or synthetic DNA encoding a part or full region of albumin.

As a method for introducing a base sequence encoding a glycosylation sequence into a DNA encoding albumin (particularly HSA) obtained as mentioned above, site-directed mutagenesis known per se (e.g., Examples below) and the like can be used. A glycosylation sequence-coding sequence may be introduced into any part of the DNA encoding albumin. In the case of site-directed mutagenesis using PCR method, wherein, for example, a base sequence encoding consensus sequence Asn-Xaa-Thr/Ser of N-linked sugar chain is introduced, the sequence is preferably introduced into a site encoding the Asn residue of a DNA encoding albumin or a site encoding the Thr or Ser residue thereof. To be specific, a base sequence encoding a consensus sequence of N-linked sugar chain can be introduced by PCR using a DNA encoding albumin as a template, and (1) an oligonucleotide complementary to a region containing a base sequence encoding any Asn-Xaa1-Xaa2 site in the albumin (provided the codon corresponding to Xaa2 is substituted by a codon encoding Thr or Ser) or (2) an oligonucleotide complementary to a region containing a base sequence encoding any Xaa1-Xaa2-Thr/Ser site in the albumin (provided the codon corresponding to Xaa1 is substituted by a codon encoding Asn) as one primer.

The glycosylation sequence can be made to be present in the DNA not only by amino acid substitution as mentioned above, but also by inserting a base sequence encoding an amino acid (or amino acid sequence) into a DNA encoding albumin or deleting a base sequence encoding an amino acid (or amino acid sequence) from the DNA by a similar method.

In the case of HSA, for example, more preferably, a consensus sequence of N-linked sugar chain can be introduced by substituting Asp residue shown by amino acid number 494 in the amino acid sequence shown in SEQ ID NO: 4 with Asn residue ($Asn^{494}$) (see SEQ ID NO: 2). Glycosylated HSA wherein a sugar chain is added to $Asn^{494}$ can be targeted to the liver at an efficiency equal to more than that of glycosylated albumin (having a number of sugar chains) obtained by conventionally known chemical modification, even though the number of sugar chain in the molecule is only one. In another preferable embodiment, a consensus sequence of N-linked sugar chain can be introduced by substituting Asp residue shown by amino acid number 63 in the amino acid sequence shown in SEQ ID NO: 4 with Asn residue ($Asn^{63}$), or by substituting Ala residue shown by amino acid number 320 with Thr or Ser residue ($Thr/Ser^{320}$) (see SEQ ID NO: 2). In a particularly preferable embodiment, glycosylated HSA of the present invention can further contain, in addition to $Asn^{494}$, one or more glycosylation sequences, preferably consensus sequence Asn-Xaa-Thr/Ser of N-linked sugar chain. As a further sugar chain addition site, the above-mentioned $Asn^{63}$ and/or $Asn^{318}$ resulting from the above-mentioned substitution with $Thr/Ser^{320}$ can be mentioned.

An expression vector containing a DNA encoding a mutant albumin containing one or more partial amino acid sequences possibly subject to a glycosylation modification by an eukaryotic cell, which has been cloned as mentioned above, can be produced by ligating the DNA to a downstream of a promoter in a suitable expression vector using a restriction enzyme and a DNA ligase.

As the expression vector, bacteriophage such as plasmid derived from *Escherichia coli* (e.g., pBR322, pBR325, pUC12, pUC13), plasmid derived from Bacillus subtilis (e.g., pUB110, pTP5, pC194), plasmid derived from yeast (e.g., pSH19, pSH15), λ-phage and the like, animal (insect) virus such as retrovirus, vaccinia virus, baculovirus and the like, pA1-11, pXT1, pRc/CMV, pRc/RSV, pcDNAI/Neo and the like are used.

The promoter may be any as long as it is an appropriate promoter corresponding to the host used for gene expression. In the present invention, any can be used as a host cell without any particular limitation as long as it has a glycosylation modification mechanism to add a sugar chain to the glycosylation sequence contained in the mutant albumin of the present invention and, for example, various eukaryotic cells such as animal cell including mammal, insect cell, plant cell, yeast cell, fungal cell and the like, or transgenic animal/plant or insect and the like can be used.

For example, when the host is a yeast, a PHO5 promoter, a PGK promoter, a GAP promoter, an ADH promoter and the like are preferable.

When the host is an animal cell, a promoter derived from cytomegalovirus (CMV) (e.g., CMV immediate-early promoter), a promoter derived from human immunodeficiency virus (HIV) (e.g., HIV LTR), a promoter derived from Rous sarcoma virus (RSV) (e.g., RSV LTR), a promoter derived from mouse mammary tumor virus (MMTV) (e.g., MMTV LTR), a promoter derived from Moloney murine leukemia virus (MoMLV) (e.g., MMTV LTR), a promoter derived from simple herpes virus (HSV) (e.g., HSV thymidine kinase (TK) promoter), a promoter derived from SV40 promoter (e.g., SV40 early promoter), a promoter derived from Epstein-Barr virus (EBV), a promoter derived from adeno-associated virus (AAV) (e.g., AAV p5 promoter), a promoter derived from adenovirus (AdV) (Ad2 or Ad5 major late promoter) and the like can be used.

When the host is an insect cell, a polyhedrin promoter, a P10 promoter and the like are preferable.

As the expression vector, besides those mentioned above, one containing an enhancer, a splicing signal, a polyA addition signal, a selection marker, an SV40 replication origin and the like on demand can be used. As the selection marker, for example, dihydrofolate reductase (dhfr) gene [methotrexate (MTX) resistance], ampicillin resistance (Amp$^r$) gene, neomycin resistance (Neo$^r$) gene (G418 resistance) and the like can be mentioned. Particularly, when dhfr-deficient Chinese hamster (CHO-dhfr$^-$) cell is used and dhfr gene is used as a selection marker, the object gene can also be selected in a thymidine-free medium. Moreover, when the DNA to be inserted does not contain an initiation codon and a stop codon, a vector containing an initiation codon (ATG or GTG) and a stop codon (TAG, TGA, TAA) at the downstream of promoter region and at the upstream of terminator region, respectively, is preferably used.

Where necessary, a base sequence encoding a signal sequence suitable for the host (signal codon) may be added to the 5' end side of a DNA encoding the mutant albumin. For example, when the host is a yeast, MFα signal sequence, SUC2 signal sequence and the like can be used. When the host is an animal cell, insulin signal sequence, α-interferon signal sequence, antibody molecule signal sequence and the like can be used. However, since native prepro-sequence of HSA (amino acid sequence shown by amino acid number –24 to –1 in the amino acid sequence shown in SEQ ID NO: 4) is known to function as a secretion signal in most heterologous eukaryotic cells, a DNA encoding prepro-HSA can also be directly inserted into an expression vector.

As mentioned above, for example, yeast, insect cell, insect, animal cell, animal and the like are used as a host.

As the yeast, for example, *Saccharomyces cerevisiae* AH22, AH22R$^-$, NA87-11A, DKD-5D, 20B-12, *Schizosaccharomyces pombe* NCYC1913, NCYC2036 and the like are used.

As the insect cell, for example, when the virus is AcNPV, established cell line derived from *Spodoptera frugiperda* larva (*Spodoptera frugiperda* cell; Sf cell), MG1 cell derived from *Trichoplusia ni* midgud, High Five™ cell derived from *Trichoplusia ni* egg, cell derived from *Mamestra brassicae*, cell derived from Estigmena acrea and the like are used. When the virus is BmNPV, established cell line derived from silkworm (*Bombyx mori* N cell; BmN cell) and the like are used as the insect cell. As the Sf cell, for example, Sf9 cell (ATCC CRL1711), Sf21 cell (both in Vaughn, J. L. et al., In Vivo, 13, 213-217 (1977)) and the like are used.

As the insect, for example, *Bombyx mori* larva and the like are used.

As the animal cell, for example, cell derived from monkey (e.g., COS-1, COS-7, CV-1, Vero), cell derived from hamster (e.g., BHK, CHO, CHO-K1, CHO-dhfr$^-$), cell derived from mouse (e.g., NIH3T3, L, L929, CTLL-2, AtT-20), cell derived from rat (e.g., H4IIE, PC-12, 3Y1, NBT-II), cell derived from human (e.g., HEK293, A549, HeLa, HepG2, HL-60, Jurkat, U937) and the like are used.

Transformation can be performed according to a known method depending on the kind of the host.

For example, yeast can be transformed according to the methods described in Methods in Enzymology, 194, 182-187 (1991), Proc. Natl. Acad. Sci. USA, 75, 1929 (1978) and the like.

For example, insect cell and insect can be transformed according to the methods described in Bio/Technology, 6, 47-55 (1988) and the like.

For example, animal cell can be transformed according to the methods described in *Saibo Kogaku, extra issue* 8, *Shin Saibo Kogaku Jikken Protocol*, 263-267 (1995) (published by Shujunsha) and Virology, 52, 456 (1973).

The transformant can be cultured according to a known method depending on the kind of the host.

As the medium, a liquid medium is preferable. The medium preferably contains a carbon source, a nitrogen source, an inorganic substance and the like necessary for the growth of the transformant. Here, as the carbon source, for example, glucose, dextrin, soluble starch, sucrose and the like can be used; as the nitrogen source, for example, inorganic or organic substances such as ammonium salts, nitrate salts, corn steep liquor, peptone, casein, meat extract, soybean cake, potato extract and the like can be used; and as the inorganic substance, for example, calcium chloride, sodium dihydrogen phosphate, magnesium chloride and the like can be used. The medium may contain a yeast extract, vitamins, a growth-promoting factor and the like. The pH of the medium is preferably about 5-8.

As a medium for cultivating a transformant whose host is a yeast, for example, Burkholder minimum medium, SD medium containing 0.5% casamino acid and the like can be mentioned. The pH of the medium is preferably about 5-8. The culture is generally performed at about 20° C.-35° C. for about 24-72 hr. Where necessary, aeration and agitation may also be performed.

As a medium for cultivating a transformant whose host is an insect cell or a insect, for example, Grace's Insect Medium appropriately supplemented with an additive such as inactivated 10% bovine serum and the like, and the like are used. The pH of the medium is preferably about 6.2-6.4. The culture is generally performed at about 27° C. for about 3-5 days. Where necessary, aeration and agitation may also be performed.

As a medium for cultivating a transformant whose host is an animal cell, for example, minimum essential medium (MEM), Dulbecco's Modified Eagle Medium (DMEM), RPMI1640 medium, 199 medium and the like supplemented with about 5-20% of fetal bovine serum are used. The pH of the medium is preferably about 6-8. The culture is generally performed at about 30° C.-40° C. for about 15-60 hr. Where necessary, aeration and agitation may also be performed.

In this manner, Glycosylated albumin can be intracellularly or extracellularly provided by a transformant.

Since the glycosylated albumin of the present invention can be preferably used as a carrier molecule capable of specific transfer to the liver, particularly kupffer's cell, one wherein a high-mannose type sugar chain having high affinity for a receptor on the cell surface is added is more preferable. Here, the "high-mannose type" means a sugar chain wherein one or more, preferably two or more, more preferably three or more, particularly preferably five or more, mannose molecules are further added to the core sugar chain (including three mannose molecules). From such aspects, a yeast cell, permitting addition of only a hyper-mannose type sugar chain and also permitting addition of a hyper-mannose type sugar chain having still more mannose molecules than those in animal cell and the like, is more preferable as a host cell, than animal cell and insect cell capable of a different glycosylation modification such as those of a complex type and a mixed type in addition to a high-mannose type. Particularly, a yeast of the genus Pichia can grow utilizing methanol as a sole carbon source, and when grown in methanol, an enzyme necessary for treating methanol and a metabolic intermediate thereof are disinhibited and expressed. It is known that the secretion expression level of a heterologous protein markedly exceeds that of *Saccharomyces* yeast when the methanol-utilizing pathway is used. In fact, production of HSA using this system is in the phase of practical application (e.g., JP-A-6-22784), where HSA of a 10 g order can be produced from 1 L of a medium. In the following, as one of the particularly preferable embodiments of the present invention, a production method of the glycosylated albumin of the present invention, which uses a *Pichia* yeast as a host cell, is explained.

The vector to be used is not particularly limited as long as it can be maintained genetically stably by autonomous replication in a fungus body of yeast of the genus *Pichia* or integration into a yeast genome. Examples of the autonomously-replicable vector include YEp vector, YRp vector, YCp vector and the like. In addition, examples of the vector to be integrated into a yeast genome include YIp vector and YRp vector.

Examples of the promoter functional in the yeast of the genus *Pichia* include promoters derived from a yeast, such as PHO5 promoter, PGK promoter, GAP promoter, ADH promoter derived from *S. cerevisiae* and the like, alcohol oxidase (AOX) 1 promoter, AOX2 promoter, dihydroxyacetone synthase promoter, P40 promoter, ADH promoter, folic acid dehydrogenase promoter derived from *P. pastoris* and the like. In addition, the above-mentioned promoter derived from a yeast may be a mutant promoter modified to further improve the gene expression efficiency, for example, mutant AOX2 (mAOX2) promoter [Ohi et al., Mol. Gen. Genet., 243, 489-499 (1994); JP-A-4-299984] and the like. Preferably, the promoter is a promoter of an enzyme gene necessary for treating methanol or a metabolic intermediate thereof, in order to use a methanol-metabolizing system in the yeast of the genus *Pichia*, such as AOX1 promoter, mAOX2 promoter and the like.

The expression vector containing the DNA encoding mutant albumin of the present invention preferably further contains transcription terminator sequence (terminator) functional in a yeast of the genus *Pichia* (e.g., AOX1 terminator etc.), enhancer sequence, selection marker gene usable for selecting yeast (auxotrophic gene, for example, HIS4, LEU2, ARG4 and URA3 gene derived from *P. pastoris* or *S. cerevisiae*, and the like, or antibiotic resistance gene, for example, resistance gene to cycloheximide, G-418, chloramphenicol, bleomycin, hygromycin etc., and the like) and the like, and when desired, may contain replicable unit functional in yeast. For preparation of the vector in a large amount, moreover, the vector more preferably contains a replicable unit functional in *Escherichia coli* and a selection marker gene usable for selecting *Escherichia coli* (e.g., resistance gene to ampicillin and tetracycline etc.)

When the expression vector is of a type incorporated into a yeast genome, the vector preferably further contains a sequence homologous to a yeast genome necessary for homologous recombination. As such homology sequence, the aforementioned auxotrophic gene sequence can be mentioned. Accordingly, in one preferable embodiment, the expression vector of the present invention is one wherein an expression cassette of the above-mentioned mutant albumin is inserted in an auxotrophic gene (in the present specification, the "expression cassette" means a unit enabling gene expression, whose minimal unit is a protein-coding sequence configured under regulation of a promoter, with preference given to a unit comprising promoter-protein-coding region-terminator).

The expression vector obtained as mentioned above can be introduced into the fungus body of the target yeast of the genus *Pichia* using, for example, a known transformation technique such as competent cell method, protoplast method, calcium phosphate coprecipitation method, polyethylene glycol method, lithium method, electroporation method, microinjection method, liposome fusion method, particle gun method and the like.

While the yeast of the genus *Pichia* to be used in the present invention is not particularly limited, for example, *P. pastoris, Pichia acaciae, Pichia angusta, Pichia anomala, Pichia capsulata, Pichia ciferrii, Pichia etchellsii, Pichia fabianii, Pichia farinosa, Pichia guilliermondii, Pichia inositovora, Pichia jadinii, Pichia methanolica, Pichia norvegensis; Pichia ofunaensis, Pichia pinus* and the like can be used. Preferred is *P. pastoris*, particularly, auxotrophic mutant *P. pastoris* strain (e.g., *P. pastoris* GTS115 strain (HIS4$^-$) [NNRL Y-15851], *P. pastoris* GS190 strain (ARG4$^-$) [NNRLY-1801], *P. pastoris* PPF1 (HIS4$^-$, URA4$^-$) [NNRL Y-18017] and the like).

By cultivating the transformed yeast of the genus *Pichia* by a method generally used in the art, glycosylated albumin can be produced. The medium to be used needs to contain at least a carbon source and an inorganic or organic nitrogen source necessary for the growth of the host cell. Examples of the carbon source include methanol, glycerol, glucose, sucrose, dextran, soluble starch and the like. In addition, examples of the inorganic or organic nitrogen source include ammonium salts, nitrate salts, amino acid, corn steep liquor, peptone, casein, meat extract, yeast extract, soybean cake, potato extract and the like. When desired, moreover, other nutrients, for example, inorganic salts such as calcium chloride, sodium dihydrogenphosphate, magnesium chloride and the like, vitamins such as biotin and the like, antibiotic and the like can be added.

Examples of the medium to be used include conventional natural medium (e.g., YPD medium, YPM medium, YPG medium etc.) and synthetic medium. As the pH and culture temperature of the medium, those suitable for the growth of yeast and production of albumin are employed. For example, pH of about 5—about 8 and culture temperature of about 20° C.—about 30° C. are preferable. In addition, aeration and agitation are performed as necessary. The culture is generally performed for about 48—about 120 hr.

For example, when a promoter whose expression is induced by methanol, such as AOX1 promoter, mAOX2 promoter and the like, is used as a promoter functional in the fungus body of a yeast of the genus *Pichia*, a method of liquid aeration-agitation culture using natural medium controlled to pH about 6.0, which contains glycerol as a carbon source for the growth of fungus body and methanol as albumin expression inducer is most preferable. When the expression of albumin is not preferable for the growth of fungus body, a method including first increasing the amount of fungus body with a carbon source other than methanol, and inducing the expression of albumin by addition of methanol is more preferable. In a culture in a jarfermenter, moreover, a high density culture method is suitable for the production of albumin. The culture may be performed by any of batch culture, feeding culture and continuous culture, with preference given to feeding culture method. That is, for a certain period, a method including culturing the host fungus body in a medium (initial medium) containing a carbon energy source suitable for the growth (e.g., glucose etc.) and/or a nutrient source, and confining albumin in the system until completion of the culture while additionally supplying a substrate controlling the growth of the host cell (that is, methanol) to the medium from a certain point in time according to the situation can be used (see e.g., JP-A-3-83595).

Albumin produced in the culture can be isolated and purified by centrifugation and/or filtration of the culture after completion of the culture to give a culture supernatant (in the case of secretory expression) or fungus body of yeast (in the case of expression in fungus body), which is then treated according to a method known per se. As such method, a method utilizing the solubility such as salting out, solvent precipitation and the like; a method mainly utilizing difference in the molecular weight such as dialysis, ultrafiltration, gel filtration method, SDS-polyacrylamide gel electrophoresis and the like; a method utilizing difference in the electric charge such as ion exchange chromatography and the like; a method utilizing specific affinity such as affinity chromatography and the like; a method utilizing difference in hydrophobicity such as reversed-phase high performance liquid chromatography and the like; a method utilizing difference in the isoelectric point such as isoelectric focusing and the like; and the like can be used. These methods can be appropriately combined.

Examples of a method for confirming the isolated and purified glycosylated albumin include known Western blotting method and the like. In addition, the structure of the purified glycosylated albumin can be clarified by amino acid analysis, N-terminal amino acid sequence, primary structure analysis, sugar chain analysis and the like.

The thus-obtained glycosylated albumin is a uniform glycoprotein wherein a sugar chain, preferably a high-mannose type sugar chain, is selectively added to the glycosylation sequence of a mutant albumin, and therefore shows high transferability to the nonparenchymal cells of the liver, particularly kupffer's cell. Accordingly, the present invention also provides a drug carrier to the liver, which contains the above-mentioned glycosylated albumin of the present invention.

Since the drug carrier of the present invention, which contains the glycosylated albumin of the present invention (particularly HSA) as a main component, can be utilized for targeting any pharmaceutical compound that becomes effective for the prophylaxis and/or treatment on delivery to the liver, preferably hepatic nonparenchymal cells, particularly kupffer's cell, to the organ or cell. Examples of such pharmaceutical compound include antioxidative substances (e.g., N-acetylcysteine, ascorbic acid etc.), nitric oxide and the like. A preparation wherein the pharmaceutical compound is bound with the glycosylated albumin of the present invention can be used for the treatment of hepatic ischemia-reperfusion injury. Moreover, examples of other pharmaceutical compounds include a hepatic drug such as hepatic fibrosis treatment drug OK432, and the like. Since albumin itself also has an antioxidative action, it can be directly used as a pharmaceutical product having an antioxidative action.

The binding mode of glycosylated albumin and a pharmaceutical compound is not particularly limited. For example, covalent bond, hydrogen bond, hydrophobic bond and the like can be used, with preference given to a covalent bond. The method for binding albumin with a pharmaceutical compound is known and, for example, "Drug Delivery System" (1986, published by CMC) can be referred to.

A pharmaceutical compound-glycosylated albumin conjugate can be processed into a preparation by a known method (ultrafiltration, sterilizing by filtration, dispension, freeze-drying etc.) Specifically, a liquid preparation containing 5-25% of the conjugate and having a pH of about 6.4-7.4 and an osmotic pressure ratio of about 1 can be mentioned. Where necessary, the preparation can contain acetyltryptophan or a salt thereof (e.g., sodium salt) and sodium caprylate as stabilizers. The amount of the stabilizer to be added is, for example, about 0.01-0.2M, preferably about 0.02-0.05M. In addition, the sodium content is, for example, not more than 3.7 mg/ml. The timing of addition of the stabilizer is before treatment by ultrafiltration, sterilizing by filtration, dispension, freeze-drying and the like.

The medical preparation of the present invention obtained via the above-mentioned steps is considered to have an extremely slim possibility of contamination with various microorganisms. As a method for more positively securing the aseptic nature of the preparation, inactivation of contaminating microorganisms can be performed by applying a heat treatment (pasteurization) after aseptic filling.

By a heat treatment including keeping a preparation filled in a container per unit dose, irrespective of the kind of the container to be filled in, for example, for not less than about 30 min in a hot water bath at about 50° C.—about 70° C. (preferably about 60° C.), contaminating microorganisms can be inactivated sufficiently. The heating time is preferably about 30 min—about 2 hr.

The pharmaceutical preparation can be administered, for example, as an injection to human, other mammals and the like. While the dose of the preparation varies depending on the kind of pharmaceutical compound, administration route, severity of disease, animal species to be the subject of administration, and drug acceptability, body weight, age and the like of the administration subject, it is, for example, in the case of a hepatic ischemia-reperfusion injury therapeutic agent containing nitric oxide as an active ingredient, generally 0.1-30 μg/kg/day, preferably 0.5-3 μg/kg/day, in a nitric oxide amount for an adult, and about 0.1-30 mg/kg/day, preferably 0.5-3 mg/kg/day, in a glycosylated albumin amount for an adult. This amount is contained in a solution (about 5—about 10 ml), and slowly administered by an intravenous injection or drip intravenous administration.

Albumin (particularly HSA) per se can be used as a pharmaceutical agent, for example, mainly for the purpose of rapidly extending plasma during shock, supplementing the amount of circulating blood, improving hypoproteinemia, sustaining colloid osmotic pressure and the like. As specific efficacy-effect, it is effective for hypoalbuminemia due to loss of albumin (burn, nephrosis syndrome etc.) and suppression of albumin synthesis (hepatic cirrhosis etc.), hemorrhagic shock and the like. Accordingly, the glycosylated albumin of the present invention can also be used as a pharmaceutical agent for improving such disease and condition. Also in this case, albumin can be processed into an injectable preparation in the same manner as above.

While the dose of albumin preparation varies depending on the administration route, severity of disease, animal species to be the subject of administration, and drug acceptability, body weight, age and the like of the administration subject, it is generally 20-25 ml of HSA 25% solution (5-12.5 g as HSA) for a single dose to an adult, which is gradually given by intravenous injection or intravenous drip infusion.

While the present invention is explained in detail in the following by referring to Examples, the present invention is not limited by these.

EXAMPLES

Example Production of Glycosylated Albumin (1) Mutation of Albumin Gene

Using plasmid pPIC9 into which human serum albumin gene was introduced (hereinafter pPIC9-HSA) as a template, and D63N sense primer of SEQ ID NO: 5 (5'-GAGTCAGCT-GAAAATTGTAACAAATCACTTCATACCC-3') and D63N antisense primer of SEQ ID NO: 6 (5'-GGGTATGAAGT-GATTTGTTACAATTTTCAGCTGACTC-3') for preparation of $Asn^{63}$-linked glycosylated albumin, A320T sense primer of SEQ ID NO: 7 (5'-GGATGTTTGCAAAAAC-TATACTGAGGCAAAGG-3') and A320T antisense primer of SEQ ID NO: 8 (5'-CCTTTGCCTCAGTATAGTTTTTG-CAAACATCC-3') for preparation of $Asn^{318}$-linked glycosylated albumin, and D494N sense primer of SEQ ID NO: 9 (5'-GCTCTGGAAGTCAATGAAACATACGTTCCC-3') and D494N antisense primer of SEQ ID NO: 10 (5'-GG-GAACGTATGTTTCATTGACTTCCAGAGC-3') for preparation of $Asn^{494}$-linked glycosylated albumin as synthetic primers, mutations of N-linked sugar chain consensus sequences were performed (QuikChange XL Site-Directed Mutagenesis Kit, Stratagene). As for mutation reaction conditions, DNA was treated for 30 sec at 95° C., after which a 12-cycle reaction of denaturation (95° C., 30 sec), annealing (55° C., 1 min) and extension (68° C., 10 min) was performed. After the reaction, the template plasmid was digested by Dpn I, and each of obtained pPIC9-HSA(D63N), pPIC9-HSA(A320T) and pPIC9-HSA(D494N) were transfected into XL-10-Gold ultracompetent cells to perform transformation. The transformants, which were transfected with the objective plasmid pPIC9-HSA(D63N), pPIC9-HSA(A320T) or pPIC9-HSA(D494N), were screened in ampicillin-added medium, and the plasmids were purified from the obtained transformants (QIAprep Spin Miniprep Kit, manufactured by QIAGEN). Confirmation of the mutations were performed by ABI Prism 310 Genetic Analyzer (Applied Biosystems) using D63N sequence primer of SEQ ID NO: 11 (5'-GAAAATTTCGACGCCTTGGTGTTGATTGCC-3') for pPIC9-HSA(D63N), A320T sequence primer of SEQ ID NO: 12 (5'-GGCGGACCTTGCCGACTATATCTGTGA-3') for pPIC9-HSA(A320T), and D494N sequence primer of SEQ ID NO: 13 (5'-GGTCTCAAGAAACCTAG-GAAAAGTGGG-3') for pPIC9-HSA(D494N). Moreover, in order to prepare human serum albumin which was bonded by sugar chains at all three sites of $Asn^{63}$, $Asn^{318}$ and $Asn^{494}$, mutation of N-linked sugar chain consensus sequence was performed in the same way using above-prepared pPIC9-HSA(D63N) as a template, and A320T sense primer of SEQ ID NO: 7 and A320T antisense primer of SEQ ID NO: 8 as synthetic primers (QuikChange XL Site-Directed Mutagenesis Kit, Stratagene). Using thus prepared pPIC9-HSA (D63N/A320T) as a template, and D494N sense primer of SEQ ID NO: 9 and D494N antisense primer of SEQ ID NO: 10 as synthetic primers, mutation was performed (QuikChange XL Site-Directed Mutagenesis Kit, Stratagene) in the same way to prepare pPIC9-HSA(D63N/A320T/D494N).

(2) Expression of Glycosylated Human Serum Albumin

Each of pPIC9-HSA(D63N), pPIC9-HSA(A320T), pPIC9-HSA(D494N) and pPIC9-HSA(D63N/A320T/D494N) was digested with restriction enzyme Sal I, purified by phenol extraction and ethanol precipitation, and subsequently transformed into HIS4 gene locus of Pichia yeast (GS115 strain) by homologous recombination using an electroporation apparatus (Gene Pulser II Electroporation System, manufactured by BIO-RAD). The obtained transformants were cultured in BMMY liquid medium, and stocked in glycerol after confirmation of expression of albumin.

(3) Purification of Glycosylated Albumin

The transformed Pichia yeast was cultured in BMGY liquid medium for 48 hr, and subsequently in BMMY medium for 96 hr as adding 1% methanol every 12 hr. The yeast was separated by centrifugation (6,000 g×10 min.), after which the culture supernatant was dialyzed against 200 mM acetate buffer. Then, albumin was bonded to Blue Sepharose CL-6B column (manufactured by Amersham Biosciences), and eluted by concentration gradient of 0 to 3 M NaCl. Subsequently, this eluate was dialyzed against 0.65 M ammonium sulfate/100 mM sodium phosphate buffer (pH 7.0), and passed through HiTrap Phenyl HP column (manufactured by Amersham Biosciences), and the nonadsorbed fraction was recovered. After that, defatting by activated carbon was performed.

Comparative Example 1

Production of Nonglycosylated (Wild-Type) Human Serum Albumin

Manipulated in the same manner as in Example, except that mutation of N-linked sugar chain consensus sequence was not performed, nonglycosylated human serum albumin was expressed in Pichia yeast, and human serum albumin (HSA) was obtained.

(4) Experimental Example 1

Glycosylated albumin, which was prepared in the same way as in Example, was labeled with radioactive indium isotope ($^{111}$In) to prepare $^{111}$In-glycosylated albumin (D63N, A320T, D494N and D63N/A320T/D494N). $^{111}$In-glycosylated albumin was administered intravenously through the tail into a mouse (dose; 1 mg/kg), blood and liver were collected at fixed intervals after the administration, and albumin concentration and liver transfer were measured by radiation dose measuring equipment. As a control, human serum albumin obtained in Comparative Example 1 was labeled with $^{111}$In ($^{111}$In-human serum albumin), which was administered into a mouse, and measurement was carried out in the same way. Proportion of glycosylated albumin concentration in plasma and liver based on elapsed time after the administration and dose, namely transferability to liver (Hepatic accumulation (% of dose)), is shown in FIG. 1.

The result from FIG. 1 illustrates that glycosylated albumin, particularly D494N and D63N/A320T/D494N, rapidly vanishes from blood and is actively introduced to liver. Also, from the remarkable difference of in vivo kinetics among D63N, A320T and D494N, it is suggested that liver transferability of glycosylated albumin be largely dependent on the binding site of a sugar chain, in addition to the sugar density of the molecular surface so far been proposed.

(5) Experimental Example 2

Charge states of the $^{111}$In-glycosylated albumin from Example (D63N, A320T, D494N and D63N/A320T/D494N) and the human serum albumin from Comparative Example 1 were evaluated using laser electrophoresis-zeta potential analyzer (LEZA-500T). As shown in Table 1, significant difference of the charge was not found in all of the variants prepared in this study compared to nonglycosylated albumin (HSA).

From this, it can be said that albumin which has been subjected to glycosylation modification by eukaryotic cell has little difference of the charge of protein relative to the one which has not been subjected to, and sufficiently maintains its intrinsic properties of the protein.

On the other hand, when the liver transfer (Hepatic accumulation (% of dose)) at 60 min was read from FIG. 1 (Table 1), that of glycosylated albumin was 6-65 times higher than that of nonglycosylated albumin (HSA). This proved that liver transferability was enhanced while maintaining the properties of albumin protein.

TABLE 1 various albumin

| | | | | |
|---|---|---|---|---|
| derived from genetic engineering | Comparative Example 1 | HSA | −0.311 | 0.97 |
| | Example | D63N | −0.304 | 10.77 |
| | | A320T | −0.300 | 5.97 |
| | | D494N | −0.298 | 49.31 |
| | | D63N/A320T/D494N | −0.302 | 65.51 |
| chemical modification | Comparative Example 2 (non-patent reference 3) | BSA | −0.353 | 1 |
| | | Suc$_{20}$-BSA | −0.588 | 23 |
| | | Suc$_{28}$-BSA | −0.946 | 63 |
| | | Suc$_{40}$-BSA | −1.277 | 57 |
| | | Suc$_{46}$-BSA | −1.672 | 49 |
| | | Suc$_{54}$-BSA | −1.912 | 47 |

Comparative Example 2

Figure 2:
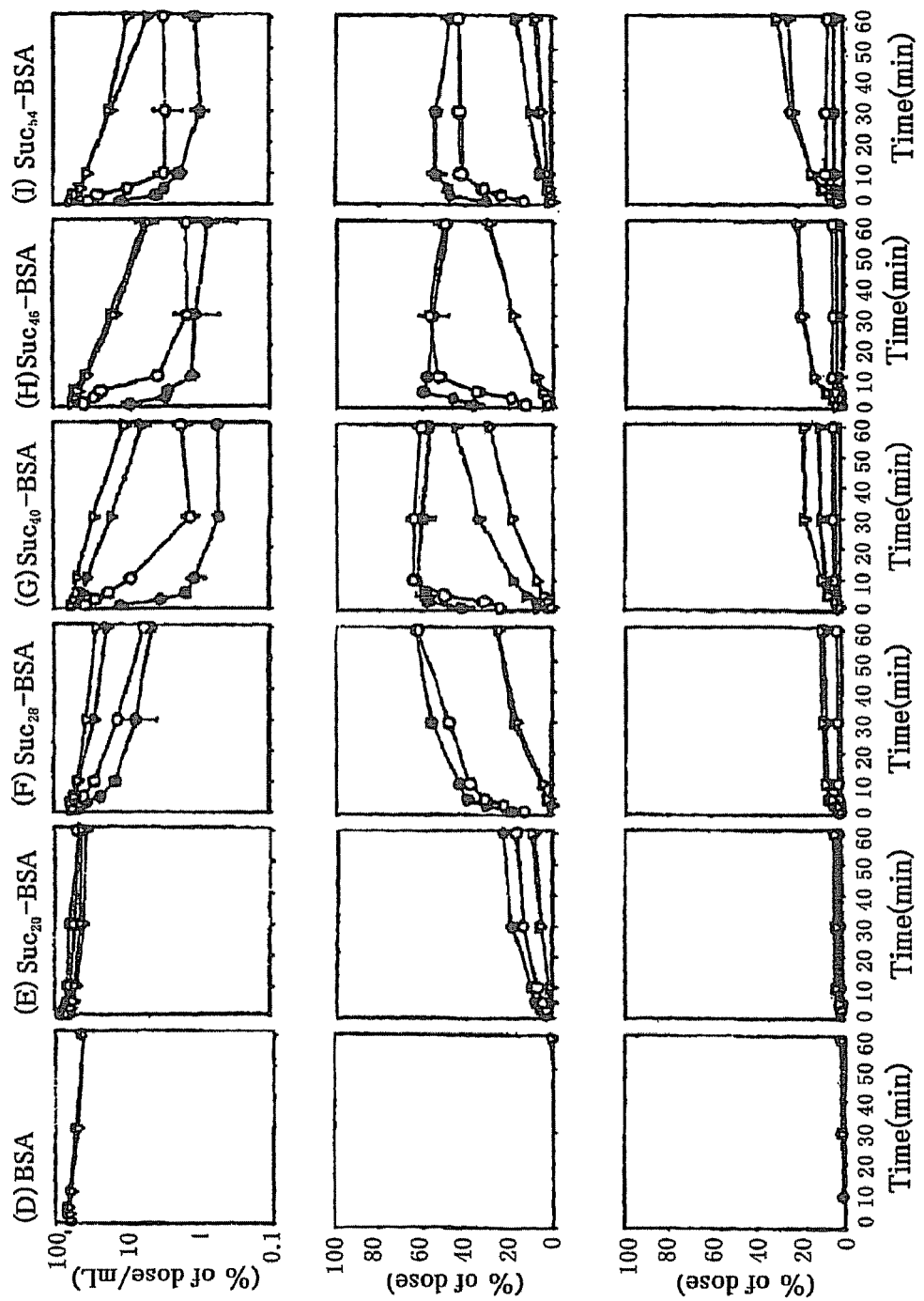
FIG. 2 is a graph showing the transfer of $^{111}$In-labeled, succinic acid-modified (Suc-)bovine serum albumin (BSA) to plasma (upper), liver (middle) and kidney (lower) when it was intravenously administered to mouse (see Takakura Y et al., Int. J. Pharm. 105: 19-29, 1994), wherein n of $Suc_n$-BSA shows the number of succinic acid bonded to BSA, ● shows 0.1 mg/kg, ○ shows 1 mg/kg, ▼ shows 10 mg/kg and ∇ shows 20 mg/kg each of BSA dose, and the presented data are an excerpt of a related portion from Takakura Y et al., Int. J. Pharm. 105: 19-29, 1994 added with the vertical axis.

Referring to figures presented in non-patent reference 3, chemically modified albumin was compared (FIG. 2, Table 1). Table 1 presents values read from FIG. 2. The chemical modification is a result of succinic acid (Suc) modification (an imide bond with ε-amino group of a Lys residue in bovine serum albumin (BSA)), and "Suc$_n$-BSA" represents a BSA to which n succinic acids are bonded.

From experiments using chemically modified albumin (BSA), it has been shown that negative-charge density on molecular surface of modified form is important for liver transfer, and thus it has been recognized until now that the greater the negative-charge becomes (the more the modification rate increases), the greater the extent of recognition by the liver becomes (see non-patent reference 3). However, the result shows that albumin modified with as much as 20 succinic acid molecules can acquire liver transferability.

On the other hand, while the charge of the non-modified BSA was about −0.35, the BSAs modified by succinic acids were not less than −0.5. Therefore, it is presumable that chemically modified albumin is heavily affected in its protein structure and function by the charge change on its molecular surface.

The glycosylated albumin of the present invention can be used as a drug carrier for DDS targeting liver nonparenchymal cells, particularly kupffer's cells. Also, utilizing gene recombinant proteins and host's glycsylation modification mechanism, uniform proteins can be produced compared to in chemical modification methods, and modification operations can be omitted. Furthermore, there is no risk of contamination of virus and the like, so it can be safely administered to living organisms for medical purposes.

While the present invention has been described with emphasis on preferred embodiments, it is obvious to those skilled in the art that the preferred embodiments can be modified. The present invention intends that the present invention can be embodied by methods other than those described in detail in the present specification. Accordingly, the present invention encompasses all modifications encompassed in the gist and scope of the appended "CLAIMS."

In addition, the contents disclosed in any publication cited herein, including patents and patent applications, are hereby incorporated in their entireties by reference, to the extent that they have been disclosed herein.

The invention claimed is:

1. An isolated glycosylated albumin protein comprising a mutant albumin and a sugar chain, wherein the mutant albumin contains one or more amino acid sequences selected from the group consisting of Asn-Xaa-Thr and Asn-Xaa-Ser, wherein Xaa is an amino acid selected from the group consisting of lysine, tyrosine, and glutamic acid, and wherein a sugar chain is bound to one or more of the amino acid sequences.

2. The protein of claim 1, which has an amino acid sequence having not less than 95% identity with the amino acid sequence of amino acid numbers 1-585 in SEQ ID NO: 2, wherein the 63rd amino acid is Asn and/or the 320th amino acid is Thr or Ser and/or the 494th amino acid is Asn.

3. The protein of claim 1, which has an amino acid sequence of amino acid numbers 1-585 in SEQ ID NO: 2, wherein the 63rd amino acid is Asn and/or the 320th amino acid is Thr or Ser and/or the 494th amino acid is Asn.

4. A pharmaceutical composition comprising the protein of claim 1.

5. The pharmaceutical composition of claim 4, further comprising a pharmaceutical compound to be delivered to the liver.

6. The pharmaceutical composition of claim 5, wherein the protein delivers the pharmaceutical compound to Kupffer's cells.

7. A pharmaceutical composition comprising the protein of claim 2.

8. The pharmaceutical composition of claim 7, further comprising a pharmaceutical compound to be delivered to the liver.

9. The pharmaceutical composition of claim 8, wherein the protein delivers the pharmaceutical compound to Kupffer's cells.

10. A pharmaceutical composition comprising the protein of claim 3.

11. The pharmaceutical composition of claim 10, further comprising a pharmaceutical compound to be delivered to the liver.

12. The pharmaceutical composition of claim 11, wherein the protein delivers the pharmaceutical compound to Kupffer's cells.

\* \* \* \* \*

SEQUENCE LISTING

```
<160> NUMBER OF SEQ ID NOS: 13

<210> SEQ ID NO 1
<211> LENGTH: 1827
<212> TYPE: DNA
<213> ORGANISM: Artificial
<220> FEATURE:
<223> OTHER INFORMATION: DNA encoding mutant HSA having glycosylation
      site(s).
<220> FEATURE:
<221> NAME/KEY: CDS
<222> LOCATION: (1)..(1827)
<220> FEATURE:
<221> NAME/KEY: sig_peptide
<222> LOCATION: (1)..(54)
<220> FEATURE:
<221> NAME/KEY: mat_peptide
<222> LOCATION: (73)..(1827)

<400> SEQUENCE: 1 atg aag tgg gta acc ttt att tcc ctt ctt ttt ctc ttt agc tcg gct      48
Met Lys Trp Val Thr Phe Ile Ser Leu Leu Phe Leu Phe Ser Ser Ala
            -20                 -15                 -10 tat tcc agg ggt gtg ttt cgt cga gat gca cac aag agt gag gtt gct      96
Tyr Ser Arg Gly Val Phe Arg Arg Asp Ala His Lys Ser Glu Val Ala
         -5                  -1   1                   5 cat cgg ttt aaa gat ttg gga gaa gaa aat ttc aaa gcc ttg gtg ttg     144
His Arg Phe Lys Asp Leu Gly Glu Glu Asn Phe Lys Ala Leu Val Leu
```

```
                10              15              20
att gcc ttt gct cag tat ctt cag cag tgt cca ttt gaa gat cat gta      192
Ile Ala Phe Ala Gln Tyr Leu Gln Gln Cys Pro Phe Glu Asp His Val
25              30              35              40 aaa tta gtg aat gaa gta act gaa ttt gca aaa aca tgt gtt gct gat      240
Lys Leu Val Asn Glu Val Thr Glu Phe Ala Lys Thr Cys Val Ala Asp
                45              50              55 gag tca gct gaa aat tgt rac aaa tca ctt cat acc ctt ttt gga gac      288
Glu Ser Ala Glu Asn Cys Xaa Lys Ser Leu His Thr Leu Phe Gly Asp
        60              65              70 aaa tta tgc aca gtt gca act ctt cgt gaa acc tat ggt gaa atg gct      336
Lys Leu Cys Thr Val Ala Thr Leu Arg Glu Thr Tyr Gly Glu Met Ala
            75              80              85 gac tgc tgt gca aaa caa gaa cct gag aga aat gaa tgc ttc ttg caa      384
Asp Cys Cys Ala Lys Gln Glu Pro Glu Arg Asn Glu Cys Phe Leu Gln
        90              95              100 cac aaa gat gac aac cca aac ctc ccc cga ttg gtg aga cca gag gtt      432
His Lys Asp Asp Asn Pro Asn Leu Pro Arg Leu Val Arg Pro Glu Val
105             110             115             120 gat gtg atg tgc act gct ttt cat gac aat gaa gag aca ttt ttg aaa      480
Asp Val Met Cys Thr Ala Phe His Asp Asn Glu Glu Thr Phe Leu Lys
                125             130             135 aaa tac tta tat gaa att gcc aga aga cat cct tac ttt tat gcc ccg      528
Lys Tyr Leu Tyr Glu Ile Ala Arg Arg His Pro Tyr Phe Tyr Ala Pro
                140             145             150 gaa ctc ctt ttc ttt gct aaa agg tat aaa gct gct ttt aca gaa tgt      576
Glu Leu Leu Phe Phe Ala Lys Arg Tyr Lys Ala Ala Phe Thr Glu Cys
            155             160             165 tgc caa gct gct gat aaa gct gcc tgc ctg ttg cca aag ctc gat gaa      624
Cys Gln Ala Ala Asp Lys Ala Ala Cys Leu Leu Pro Lys Leu Asp Glu
        170             175             180 ctt cgg gat gaa ggg aag gct tcg tct gcc aaa cag aga ctc aag tgt      672
Leu Arg Asp Glu Gly Lys Ala Ser Ser Ala Lys Gln Arg Leu Lys Cys
185             190             195             200 gcc agt ctc caa aaa ttt gga gaa aga gct ttc aaa gca tgg gca gta      720
Ala Ser Leu Gln Lys Phe Gly Glu Arg Ala Phe Lys Ala Trp Ala Val
                205             210             215 gct cgc ctg agc cag aga ttt ccc aaa gct gag ttt gca gaa gtt tcc      768
Ala Arg Leu Ser Gln Arg Phe Pro Lys Ala Glu Phe Ala Glu Val Ser
            220             225             230 aag tta gtg aca gat ctt acc aaa gtc cac acg gaa tgc tgc cat gga      816
Lys Leu Val Thr Asp Leu Thr Lys Val His Thr Glu Cys Cys His Gly
        235             240             245 gat ctg ctt gaa tgt gct gat gac agg gcg gac ctt gcc aag tat atc      864
Asp Leu Leu Glu Cys Ala Asp Asp Arg Ala Asp Leu Ala Lys Tyr Ile
250             255             260 tgt gaa aat caa gat tcg atc tcc agt aaa ctg aag gaa tgc tgt gaa      912
Cys Glu Asn Gln Asp Ser Ile Ser Ser Lys Leu Lys Glu Cys Cys Glu
265             270             275             280 aaa cct ctg ttg gaa aaa tcc cac tgc att gcc gaa gtg gaa aat gat      960
Lys Pro Leu Leu Glu Lys Ser His Cys Ile Ala Glu Val Glu Asn Asp
                285             290             295 gag atg cct gct gac ttg cct tca tta gct gct gat ttt gtt gaa agt      1008
Glu Met Pro Ala Asp Leu Pro Ser Leu Ala Ala Asp Phe Val Glu Ser
            300             305             310 aag gat gtt tgc aaa aac tat rct gag gca aag gat gtc ttc ctg ggc      1056
Lys Asp Val Cys Lys Asn Tyr Xaa Glu Ala Lys Asp Val Phe Leu Gly
        315             320             325 atg ttt ttg tat gaa tat gca aga agg cat cct gat tac tct gtc gtg      1104
Met Phe Leu Tyr Glu Tyr Ala Arg Arg His Pro Asp Tyr Ser Val Val
```

|  |  |  |  |  |  |  |  |  |  |  |  |  |  |  |  |
|---|---|---|---|---|---|---|---|---|---|---|---|---|---|---|---|
|  |  | 330 |  |  |  | 335 |  |  |  | 340 |  |  |  |  |  |
| ctg | ctg | ctg | aga | ctt | gcc | aag | aca | tat | gaa | acc | act | cta | gag | aag | tgc | 1152 |
| Leu | Leu | Leu | Arg | Leu | Ala | Lys | Thr | Tyr | Glu | Thr | Thr | Leu | Glu | Lys | Cys |  |
| 345 |  |  |  |  | 350 |  |  |  |  | 355 |  |  |  |  | 360 |  |
| tgt | gcc | gct | gca | gat | cct | cat | gaa | tgc | tat | gcc | aaa | gtg | ttc | gat | gaa | 1200 |
| Cys | Ala | Ala | Ala | Asp | Pro | His | Glu | Cys | Tyr | Ala | Lys | Val | Phe | Asp | Glu |  |
|  |  |  |  | 365 |  |  |  |  | 370 |  |  |  |  | 375 |  |  |
| ttt | aaa | cct | ctt | gtg | gaa | gag | cct | cag | aat | tta | atc | aaa | caa | aat | tgt | 1248 |
| Phe | Lys | Pro | Leu | Val | Glu | Glu | Pro | Gln | Asn | Leu | Ile | Lys | Gln | Asn | Cys |  |
|  | 380 |  |  |  |  | 385 |  |  |  |  | 390 |  |  |  |  |  |
| gag | ctt | ttt | gag | cag | ctt | gga | gag | tac | aaa | ttc | cag | aat | gcg | cta | tta | 1296 |
| Glu | Leu | Phe | Glu | Gln | Leu | Gly | Glu | Tyr | Lys | Phe | Gln | Asn | Ala | Leu | Leu |  |
|  |  | 395 |  |  |  |  | 400 |  |  |  |  | 405 |  |  |  |  |
| gtt | cgt | tac | acc | aag | aaa | gta | ccc | caa | gtg | tca | act | cca | act | ctt | gta | 1344 |
| Val | Arg | Tyr | Thr | Lys | Lys | Val | Pro | Gln | Val | Ser | Thr | Pro | Thr | Leu | Val |  |
| 410 |  |  |  |  | 415 |  |  |  |  | 420 |  |  |  |  |  |  |
| gag | gtc | tca | aga | aac | cta | gga | aaa | gtg | ggc | agc | aaa | tgt | tgt | aaa | cat | 1392 |
| Glu | Val | Ser | Arg | Asn | Leu | Gly | Lys | Val | Gly | Ser | Lys | Cys | Cys | Lys | His |  |
| 425 |  |  |  |  | 430 |  |  |  |  | 435 |  |  |  |  | 440 |  |
| cct | gaa | gca | aaa | aga | atg | ccc | tgt | gca | gaa | gac | tat | cta | tcc | gtg | gtc | 1440 |
| Pro | Glu | Ala | Lys | Arg | Met | Pro | Cys | Ala | Glu | Asp | Tyr | Leu | Ser | Val | Val |  |
|  |  |  |  | 445 |  |  |  |  | 450 |  |  |  |  | 455 |  |  |
| ctg | aac | cag | tta | tgt | gtg | ttg | cat | gag | aaa | acg | cca | gta | agt | gac | aga | 1488 |
| Leu | Asn | Gln | Leu | Cys | Val | Leu | His | Glu | Lys | Thr | Pro | Val | Ser | Asp | Arg |  |
|  | 460 |  |  |  |  | 465 |  |  |  |  | 470 |  |  |  |  |  |
| gtc | acc | aaa | tgc | tgc | aca | gaa | tcc | ttg | gtg | aac | agg | cga | cca | tgc | ttt | 1536 |
| Val | Thr | Lys | Cys | Cys | Thr | Glu | Ser | Leu | Val | Asn | Arg | Arg | Pro | Cys | Phe |  |
|  |  | 475 |  |  |  |  | 480 |  |  |  |  | 485 |  |  |  |  |
| tca | gct | ctg | gaa | gtc | rat | gaa | aca | tac | gtt | ccc | aaa | gag | ttt | aat | gct | 1584 |
| Ser | Ala | Leu | Glu | Val | Xaa | Glu | Thr | Tyr | Val | Pro | Lys | Glu | Phe | Asn | Ala |  |
| 490 |  |  |  |  | 495 |  |  |  |  | 500 |  |  |  |  |  |  |
| gaa | aca | ttc | acc | ttc | cat | gca | gat | ata | tgc | aca | ctt | tct | gag | aag | gag | 1632 |
| Glu | Thr | Phe | Thr | Phe | His | Ala | Asp | Ile | Cys | Thr | Leu | Ser | Glu | Lys | Glu |  |
| 505 |  |  |  |  | 510 |  |  |  |  | 515 |  |  |  |  | 520 |  |
| aga | caa | atc | aag | aaa | caa | act | gca | ctt | gtt | gag | ctc | gtg | aaa | cac | aag | 1680 |
| Arg | Gln | Ile | Lys | Lys | Gln | Thr | Ala | Leu | Val | Glu | Leu | Val | Lys | His | Lys |  |
|  |  |  |  | 525 |  |  |  |  | 530 |  |  |  |  | 535 |  |  |
| ccc | aag | gca | aca | aaa | gag | caa | ctg | aaa | gct | gtt | atg | gat | gat | ttc | gca | 1728 |
| Pro | Lys | Ala | Thr | Lys | Glu | Gln | Leu | Lys | Ala | Val | Met | Asp | Asp | Phe | Ala |  |
|  |  |  | 540 |  |  |  |  | 545 |  |  |  |  | 550 |  |  |  |
| gct | ttt | gta | gag | aag | tgc | tgc | aag | gct | gac | gat | aag | gag | acc | tgc | ttt | 1776 |
| Ala | Phe | Val | Glu | Lys | Cys | Cys | Lys | Ala | Asp | Asp | Lys | Glu | Thr | Cys | Phe |  |
|  |  | 555 |  |  |  |  | 560 |  |  |  |  | 565 |  |  |  |  |
| gcc | gag | gag | ggt | aaa | aaa | ctt | gtt | gct | gca | agt | caa | gct | gcc | tta | ggc | 1824 |
| Ala | Glu | Glu | Gly | Lys | Lys | Leu | Val | Ala | Ala | Ser | Gln | Ala | Ala | Leu | Gly |  |
| 570 |  |  |  |  | 575 |  |  |  |  | 580 |  |  |  |  |  |  |
| tta |  |  |  |  |  |  |  |  |  |  |  |  |  |  |  | 1827 |
| Leu |  |  |  |  |  |  |  |  |  |  |  |  |  |  |  |  |
| 585 |  |  |  |  |  |  |  |  |  |  |  |  |  |  |  |  |

```
<210> SEQ ID NO 2
<211> LENGTH: 609
<212> TYPE: PRT
<213> ORGANISM: Artificial
<220> FEATURE:
<221> NAME/KEY: misc_feature
<222> LOCATION: (63)..(63)
<223> OTHER INFORMATION: The 'Xaa' at location 63 stands for Asp, or
      Asn.
<220> FEATURE:
<221> NAME/KEY: misc_feature
<222> LOCATION: (320)..(320)
<223> OTHER INFORMATION: The 'Xaa' at location 320 stands for Ala, or
```

```
        Thr.
<220> FEATURE:
<221> NAME/KEY: misc_feature
<222> LOCATION: (494)..(494)
<223> OTHER INFORMATION: The 'Xaa' at location 494 stands for Asp, or
      Asn.
<220> FEATURE:
<223> OTHER INFORMATION: Synthetic Construct

<400> SEQUENCE: 2

Met Lys Trp Val Thr Phe Ile Ser Leu Leu Phe Leu Phe Ser Ser Ala
                -20                 -15                 -10

Tyr Ser Arg Gly Val Phe Arg Arg Asp Ala His Lys Ser Glu Val Ala
            -5              -1   1                   5

His Arg Phe Lys Asp Leu Gly Glu Glu Asn Phe Lys Ala Leu Val Leu
 10                      15                  20

Ile Ala Phe Ala Gln Tyr Leu Gln Gln Cys Pro Phe Glu Asp His Val
 25                  30              35                  40

Lys Leu Val Asn Glu Val Thr Glu Phe Ala Lys Thr Cys Val Ala Asp
                 45                  50                  55

Glu Ser Ala Glu Asn Cys Xaa Lys Ser Leu His Thr Leu Phe Gly Asp
             60                  65                  70

Lys Leu Cys Thr Val Ala Thr Leu Arg Glu Thr Tyr Gly Glu Met Ala
             75                  80                  85

Asp Cys Cys Ala Lys Gln Glu Pro Glu Arg Asn Glu Cys Phe Leu Gln
             90                  95                 100

His Lys Asp Asp Asn Pro Asn Leu Pro Arg Leu Val Arg Pro Glu Val
105                 110                 115                 120

Asp Val Met Cys Thr Ala Phe His Asp Asn Glu Glu Thr Phe Leu Lys
                125                 130                 135

Lys Tyr Leu Tyr Glu Ile Ala Arg Arg His Pro Tyr Phe Tyr Ala Pro
                140                 145                 150

Glu Leu Leu Phe Phe Ala Lys Arg Tyr Lys Ala Ala Phe Thr Glu Cys
                155                 160                 165

Cys Gln Ala Ala Asp Lys Ala Ala Cys Leu Leu Pro Lys Leu Asp Glu
            170                 175                 180

Leu Arg Asp Glu Gly Lys Ala Ser Ser Ala Lys Gln Arg Leu Lys Cys
185                 190                 195                 200

Ala Ser Leu Gln Lys Phe Gly Glu Arg Ala Phe Lys Ala Trp Ala Val
                205                 210                 215

Ala Arg Leu Ser Gln Arg Phe Pro Lys Ala Glu Phe Ala Glu Val Ser
            220                 225                 230

Lys Leu Val Thr Asp Leu Thr Lys Val His Thr Glu Cys Cys His Gly
            235                 240                 245

Asp Leu Leu Glu Cys Ala Asp Asp Arg Ala Asp Leu Ala Lys Tyr Ile
250                 255                 260

Cys Glu Asn Gln Asp Ser Ile Ser Ser Lys Leu Lys Glu Cys Cys Glu
265                 270                 275                 280

Lys Pro Leu Leu Glu Lys Ser His Cys Ile Ala Glu Val Glu Asn Asp
                285                 290                 295

Glu Met Pro Ala Asp Leu Pro Ser Leu Ala Ala Asp Phe Val Glu Ser
                300                 305                 310

Lys Asp Val Cys Lys Asn Tyr Xaa Glu Ala Lys Asp Val Phe Leu Gly
            315                 320                 325

Met Phe Leu Tyr Glu Tyr Ala Arg Arg His Pro Asp Tyr Ser Val Val
330                 335                 340
```

```
                                    -continued

Leu Leu Leu Arg Leu Ala Lys Thr Tyr Glu Thr Thr Leu Glu Lys Cys
345                 350                 355                 360

Cys Ala Ala Ala Asp Pro His Glu Cys Tyr Ala Lys Val Phe Asp Glu
                365                 370                 375

Phe Lys Pro Leu Val Glu Glu Pro Gln Asn Leu Ile Lys Gln Asn Cys
            380                 385                 390

Glu Leu Phe Glu Gln Leu Gly Glu Tyr Lys Phe Gln Asn Ala Leu Leu
        395                 400                 405

Val Arg Tyr Thr Lys Lys Val Pro Gln Val Ser Thr Pro Thr Leu Val
    410                 415                 420

Glu Val Ser Arg Asn Leu Gly Lys Val Gly Ser Lys Cys Cys Lys His
425                 430                 435                 440

Pro Glu Ala Lys Arg Met Pro Cys Ala Glu Asp Tyr Leu Ser Val Val
                445                 450                 455

Leu Asn Gln Leu Cys Val Leu His Glu Lys Thr Pro Val Ser Asp Arg
                460                 465                 470

Val Thr Lys Cys Cys Thr Glu Ser Leu Val Asn Arg Arg Pro Cys Phe
            475                 480                 485

Ser Ala Leu Glu Val Xaa Glu Thr Tyr Val Pro Lys Glu Phe Asn Ala
        490                 495                 500

Glu Thr Phe Thr Phe His Ala Asp Ile Cys Thr Leu Ser Glu Lys Glu
505                 510                 515                 520

Arg Gln Ile Lys Lys Gln Thr Ala Leu Val Glu Leu Val Lys His Lys
                525                 530                 535

Pro Lys Ala Thr Lys Glu Gln Leu Lys Ala Val Met Asp Asp Phe Ala
            540                 545                 550

Ala Phe Val Glu Lys Cys Cys Lys Ala Asp Asp Lys Glu Thr Cys Phe
        555                 560                 565

Ala Glu Glu Gly Lys Lys Leu Val Ala Ala Ser Gln Ala Ala Leu Gly
    570                 575                 580

Leu
585

<210> SEQ ID NO 3
<211> LENGTH: 1827
<212> TYPE: DNA
<213> ORGANISM: Homo sapiens
<220> FEATURE:
<221> NAME/KEY: CDS
<222> LOCATION: (1)..(1827)
<220> FEATURE:
<221> NAME/KEY: sig_peptide
<222> LOCATION: (1)..(54)
<220> FEATURE:
<221> NAME/KEY: mat_peptide
<222> LOCATION: (73)..(1827)

<400> SEQUENCE: 3 atg aag tgg gta acc ttt att tcc ctt ctt ttt ctc ttt agc tcg gct      48
Met Lys Trp Val Thr Phe Ile Ser Leu Leu Phe Leu Phe Ser Ser Ala
        -20                 -15                 -10 tat tcc agg ggt gtg ttt cgt cga gat gca cac aag agt gag gtt gct      96
Tyr Ser Arg Gly Val Phe Arg Arg Asp Ala His Lys Ser Glu Val Ala
    -5                  -1   1               5 cat cgg ttt aaa gat ttg gga gaa gaa aat ttc aaa gcc ttg gtg ttg     144
His Arg Phe Lys Asp Leu Gly Glu Glu Asn Phe Lys Ala Leu Val Leu
        10                  15                  20 att gcc ttt gct cag tat ctt cag cag tgt cca ttt gaa gat cat gta     192
Ile Ala Phe Ala Gln Tyr Leu Gln Gln Cys Pro Phe Glu Asp His Val
25                   30                  35                  40
```

```
                                                              -continued aaa tta gtg aat gaa gta act gaa ttt gca aaa aca tgt gtt gct gat     240
Lys Leu Val Asn Glu Val Thr Glu Phe Ala Lys Thr Cys Val Ala Asp
             45                  50                  55 gag tca gct gaa aat tgt gac aaa tca ctt cat acc ctt ttt gga gac     288
Glu Ser Ala Glu Asn Cys Asp Lys Ser Leu His Thr Leu Phe Gly Asp
         60                  65                  70 aaa tta tgc aca gtt gca act ctt cgt gaa acc tat ggt gaa atg gct     336
Lys Leu Cys Thr Val Ala Thr Leu Arg Glu Thr Tyr Gly Glu Met Ala
     75                  80                  85 gac tgc tgt gca aaa caa gaa cct gag aga aat gaa tgc ttc ttg caa     384
Asp Cys Cys Ala Lys Gln Glu Pro Glu Arg Asn Glu Cys Phe Leu Gln
 90                  95                 100 cac aaa gat gac aac cca aac ctc ccc cga ttg gtg aga cca gag gtt     432
His Lys Asp Asp Asn Pro Asn Leu Pro Arg Leu Val Arg Pro Glu Val
105                 110                 115                 120 gat gtg atg tgc act gct ttt cat gac aat gaa gag aca ttt ttg aaa     480
Asp Val Met Cys Thr Ala Phe His Asp Asn Glu Glu Thr Phe Leu Lys
                125                 130                 135 aaa tac tta tat gaa att gcc aga aga cat cct tac ttt tat gcc ccg     528
Lys Tyr Leu Tyr Glu Ile Ala Arg Arg His Pro Tyr Phe Tyr Ala Pro
            140                 145                 150 gaa ctc ctt ttc ttt gct aaa agg tat aaa gct gct ttt aca gaa tgt     576
Glu Leu Leu Phe Phe Ala Lys Arg Tyr Lys Ala Ala Phe Thr Glu Cys
        155                 160                 165 tgc caa gct gct gat aaa gct gcc tgc ctg ttg cca aag ctc gat gaa     624
Cys Gln Ala Ala Asp Lys Ala Ala Cys Leu Leu Pro Lys Leu Asp Glu
    170                 175                 180 ctt cgg gat gaa ggg aag gct tcg tct gcc aaa cag aga ctc aag tgt     672
Leu Arg Asp Glu Gly Lys Ala Ser Ser Ala Lys Gln Arg Leu Lys Cys
185                 190                 195                 200 gcc agt ctc caa aaa ttt gga gaa aga gct ttc aaa gca tgg gca gta     720
Ala Ser Leu Gln Lys Phe Gly Glu Arg Ala Phe Lys Ala Trp Ala Val
                205                 210                 215 gct cgc ctg agc cag aga ttt ccc aaa gct gag ttt gca gaa gtt tcc     768
Ala Arg Leu Ser Gln Arg Phe Pro Lys Ala Glu Phe Ala Glu Val Ser
            220                 225                 230 aag tta gtg aca gat ctt acc aaa gtc cac acg gaa tgc tgc cat gga     816
Lys Leu Val Thr Asp Leu Thr Lys Val His Thr Glu Cys Cys His Gly
        235                 240                 245 gat ctg ctt gaa tgt gct gat gac agg gcg gac ctt gcc aag tat atc     864
Asp Leu Leu Glu Cys Ala Asp Asp Arg Ala Asp Leu Ala Lys Tyr Ile
    250                 255                 260 tgt gaa aat caa gat tcg atc tcc agt aaa ctg aag gaa tgc tgt gaa     912
Cys Glu Asn Gln Asp Ser Ile Ser Ser Lys Leu Lys Glu Cys Cys Glu
265                 270                 275                 280 aaa cct ctg ttg gaa aaa tcc cac tgc att gcc gaa gtg gaa aat gat     960
Lys Pro Leu Leu Glu Lys Ser His Cys Ile Ala Glu Val Glu Asn Asp
                285                 290                 295 gag atg cct gct gac ttg cct tca tta gct gct gat ttt gtt gaa agt    1008
Glu Met Pro Ala Asp Leu Pro Ser Leu Ala Ala Asp Phe Val Glu Ser
            300                 305                 310 aag gat gtt tgc aaa aac tat gct gag gca aag gat gtc ttc ctg ggc    1056
Lys Asp Val Cys Lys Asn Tyr Ala Glu Ala Lys Asp Val Phe Leu Gly
        315                 320                 325 atg ttt ttg tat gaa tat gca aga agg cat cct gat tac tct gtc gtg    1104
Met Phe Leu Tyr Glu Tyr Ala Arg Arg His Pro Asp Tyr Ser Val Val
    330                 335                 340 ctg ctg ctg aga ctt gcc aag aca tat gaa acc act cta gag aag tgc    1152
Leu Leu Leu Arg Leu Ala Lys Thr Tyr Glu Thr Thr Leu Glu Lys Cys
345                 350                 355                 360
```

| | | | | | | | | | | | | | | |
|---|---|---|---|---|---|---|---|---|---|---|---|---|---|---|
| tgt | gcc | gct | gca | gat | cct | cat | gaa | tgc | tat | gcc | aaa | gtg | ttc | gat | gaa | 1200 |
| Cys | Ala | Ala | Ala | Asp | Pro | His | Glu | Cys | Tyr | Ala | Lys | Val | Phe | Asp | Glu | |
| | | | 365 | | | | | 370 | | | | | 375 | | | |

| ttt | aaa | cct | ctt | gtg | gaa | gag | cct | cag | aat | tta | atc | aaa | caa | aat | tgt | 1248 |
| Phe | Lys | Pro | Leu | Val | Glu | Glu | Pro | Gln | Asn | Leu | Ile | Lys | Gln | Asn | Cys | |
| | 380 | | | | | 385 | | | | | 390 | | | | | |

| gag | ctt | ttt | gag | cag | ctt | gga | gag | tac | aaa | ttc | cag | aat | gcg | cta | tta | 1296 |
| Glu | Leu | Phe | Glu | Gln | Leu | Gly | Glu | Tyr | Lys | Phe | Gln | Asn | Ala | Leu | Leu | |
| | | 395 | | | | | 400 | | | | | 405 | | | | |

| gtt | cgt | tac | acc | aag | aaa | gta | ccc | caa | gtg | tca | act | cca | act | ctt | gta | 1344 |
| Val | Arg | Tyr | Thr | Lys | Lys | Val | Pro | Gln | Val | Ser | Thr | Pro | Thr | Leu | Val | |
| | 410 | | | | | 415 | | | | | 420 | | | | | |

| gag | gtc | tca | aga | aac | cta | gga | aaa | gtg | ggc | agc | aaa | tgt | tgt | aaa | cat | 1392 |
| Glu | Val | Ser | Arg | Asn | Leu | Gly | Lys | Val | Gly | Ser | Lys | Cys | Cys | Lys | His | |
| 425 | | | | | 430 | | | | | 435 | | | | | 440 | |

| cct | gaa | gca | aaa | aga | atg | ccc | tgt | gca | gaa | gac | tat | cta | tcc | gtg | gtc | 1440 |
| Pro | Glu | Ala | Lys | Arg | Met | Pro | Cys | Ala | Glu | Asp | Tyr | Leu | Ser | Val | Val | |
| | | | 445 | | | | | 450 | | | | | 455 | | | |

| ctg | aac | cag | tta | tgt | gtg | ttg | cat | gag | aaa | acg | cca | gta | agt | gac | aga | 1488 |
| Leu | Asn | Gln | Leu | Cys | Val | Leu | His | Glu | Lys | Thr | Pro | Val | Ser | Asp | Arg | |
| | | 460 | | | | | 465 | | | | | 470 | | | | |

| gtc | acc | aaa | tgc | tgc | aca | gaa | tcc | ttg | gtg | aac | agg | cga | cca | tgc | ttt | 1536 |
| Val | Thr | Lys | Cys | Cys | Thr | Glu | Ser | Leu | Val | Asn | Arg | Arg | Pro | Cys | Phe | |
| | 475 | | | | | 480 | | | | | 485 | | | | | |

| tca | gct | ctg | gaa | gtc | gat | gaa | aca | tac | gtt | ccc | aaa | gag | ttt | aat | gct | 1584 |
| Ser | Ala | Leu | Glu | Val | Asp | Glu | Thr | Tyr | Val | Pro | Lys | Glu | Phe | Asn | Ala | |
| | 490 | | | | | 495 | | | | | 500 | | | | | |

| gaa | aca | ttc | acc | ttc | cat | gca | gat | ata | tgc | aca | ctt | tct | gag | aag | gag | 1632 |
| Glu | Thr | Phe | Thr | Phe | His | Ala | Asp | Ile | Cys | Thr | Leu | Ser | Glu | Lys | Glu | |
| 505 | | | | | 510 | | | | | 515 | | | | | 520 | |

| aga | caa | atc | aag | aaa | caa | act | gca | ctt | gtt | gag | ctc | gtg | aaa | cac | aag | 1680 |
| Arg | Gln | Ile | Lys | Lys | Gln | Thr | Ala | Leu | Val | Glu | Leu | Val | Lys | His | Lys | |
| | | | 525 | | | | | 530 | | | | | 535 | | | |

| ccc | aag | gca | aca | aaa | gag | caa | ctg | aaa | gct | gtt | atg | gat | gat | ttc | gca | 1728 |
| Pro | Lys | Ala | Thr | Lys | Glu | Gln | Leu | Lys | Ala | Val | Met | Asp | Asp | Phe | Ala | |
| | | 540 | | | | | 545 | | | | | 550 | | | | |

| gct | ttt | gta | gag | aag | tgc | tgc | aag | gct | gac | gat | aag | gag | acc | tgc | ttt | 1776 |
| Ala | Phe | Val | Glu | Lys | Cys | Cys | Lys | Ala | Asp | Asp | Lys | Glu | Thr | Cys | Phe | |
| | 555 | | | | | 560 | | | | | 565 | | | | | |

| gcc | gag | gag | ggt | aaa | aaa | ctt | gtt | gct | gca | agt | caa | gct | gcc | tta | ggc | 1824 |
| Ala | Glu | Glu | Gly | Lys | Lys | Leu | Val | Ala | Ala | Ser | Gln | Ala | Ala | Leu | Gly | |
| | 570 | | | | | 575 | | | | | 580 | | | | | |

| tta | | | | | | | | | | | | | | | | 1827 |
| Leu | | | | | | | | | | | | | | | | |
| 585 | | | | | | | | | | | | | | | | |

<210> SEQ ID NO 4
<211> LENGTH: 609
<212> TYPE: PRT
<213> ORGANISM: Homo sapiens

<400> SEQUENCE: 4

Met Lys Trp Val Thr Phe Ile Ser Leu Leu Phe Leu Phe Ser Ser Ala
                  -20                 -15                 -10

Tyr Ser Arg Gly Val Phe Arg Arg Asp Ala His Lys Ser Glu Val Ala
              -5                  -1  1               5

His Arg Phe Lys Asp Leu Gly Glu Glu Asn Phe Lys Ala Leu Val Leu
         10                  15                  20

Ile Ala Phe Ala Gln Tyr Leu Gln Gln Cys Pro Phe Glu Asp His Val
 25                  30                  35                  40

```
Lys Leu Val Asn Glu Val Thr Glu Phe Ala Lys Thr Cys Val Ala Asp
            45                  50                  55

Glu Ser Ala Glu Asn Cys Asp Lys Ser Leu His Thr Leu Phe Gly Asp
            60                  65                  70

Lys Leu Cys Thr Val Ala Thr Leu Arg Glu Thr Tyr Gly Glu Met Ala
            75                  80                  85

Asp Cys Cys Ala Lys Gln Glu Pro Glu Arg Asn Glu Cys Phe Leu Gln
 90                  95                  100

His Lys Asp Asp Asn Pro Asn Leu Pro Arg Leu Val Arg Pro Glu Val
105                 110                 115                 120

Asp Val Met Cys Thr Ala Phe His Asp Asn Glu Glu Thr Phe Leu Lys
                125                 130                 135

Lys Tyr Leu Tyr Glu Ile Ala Arg Arg His Pro Tyr Phe Tyr Ala Pro
            140                 145                 150

Glu Leu Leu Phe Phe Ala Lys Arg Tyr Lys Ala Ala Phe Thr Glu Cys
            155                 160                 165

Cys Gln Ala Ala Asp Lys Ala Ala Cys Leu Leu Pro Lys Leu Asp Glu
        170                 175                 180

Leu Arg Asp Glu Gly Lys Ala Ser Ser Ala Lys Gln Arg Leu Lys Cys
185                 190                 195                 200

Ala Ser Leu Gln Lys Phe Gly Glu Arg Ala Phe Lys Ala Trp Ala Val
                205                 210                 215

Ala Arg Leu Ser Gln Arg Phe Pro Lys Ala Glu Phe Ala Glu Val Ser
            220                 225                 230

Lys Leu Val Thr Asp Leu Thr Lys Val His Thr Glu Cys Cys His Gly
            235                 240                 245

Asp Leu Leu Glu Cys Ala Asp Asp Arg Ala Asp Leu Ala Lys Tyr Ile
        250                 255                 260

Cys Glu Asn Gln Asp Ser Ile Ser Ser Lys Leu Lys Glu Cys Cys Glu
265                 270                 275                 280

Lys Pro Leu Leu Glu Lys Ser His Cys Ile Ala Glu Val Glu Asn Asp
                285                 290                 295

Glu Met Pro Ala Asp Leu Pro Ser Leu Ala Ala Asp Phe Val Glu Ser
            300                 305                 310

Lys Asp Val Cys Lys Asn Tyr Ala Glu Ala Lys Asp Val Phe Leu Gly
            315                 320                 325

Met Phe Leu Tyr Glu Tyr Ala Arg Arg His Pro Asp Tyr Ser Val Val
330                 335                 340

Leu Leu Leu Arg Leu Ala Lys Thr Tyr Glu Thr Thr Leu Glu Lys Cys
345                 350                 355                 360

Cys Ala Ala Ala Asp Pro His Glu Cys Tyr Ala Lys Val Phe Asp Glu
                365                 370                 375

Phe Lys Pro Leu Val Glu Glu Pro Gln Asn Leu Ile Lys Gln Asn Cys
            380                 385                 390

Glu Leu Phe Glu Gln Leu Gly Glu Tyr Lys Phe Gln Asn Ala Leu Leu
            395                 400                 405

Val Arg Tyr Thr Lys Lys Val Pro Gln Val Ser Thr Pro Thr Leu Val
            410                 415                 420

Glu Val Ser Arg Asn Leu Gly Lys Val Gly Ser Lys Cys Cys Lys His
425                 430                 435                 440

Pro Glu Ala Lys Arg Met Pro Cys Ala Glu Asp Tyr Leu Ser Val Val
                445                 450                 455

Leu Asn Gln Leu Cys Val Leu His Glu Lys Thr Pro Val Ser Asp Arg
```

-continued

```
                460                 465                 470
Val Thr Lys Cys Cys Thr Glu Ser Leu Val Asn Arg Arg Pro Cys Phe
        475                 480                 485
Ser Ala Leu Glu Val Asp Glu Thr Tyr Val Pro Lys Glu Phe Asn Ala
        490                 495                 500
Glu Thr Phe Thr Phe His Ala Asp Ile Cys Thr Leu Ser Glu Lys Glu
505                 510                 515                 520
Arg Gln Ile Lys Lys Gln Thr Ala Leu Val Glu Leu Val Lys His Lys
                525                 530                 535
Pro Lys Ala Thr Lys Glu Gln Leu Lys Ala Val Met Asp Asp Phe Ala
        540                 545                 550
Ala Phe Val Glu Lys Cys Cys Lys Ala Asp Asp Lys Glu Thr Cys Phe
        555                 560                 565
Ala Glu Glu Gly Lys Lys Leu Val Ala Ala Ser Gln Ala Ala Leu Gly
        570                 575                 580
Leu
585

<210> SEQ ID NO 5
<211> LENGTH: 37
<212> TYPE: DNA
<213> ORGANISM: Artificial
<220> FEATURE:
<223> OTHER INFORMATION: Primer

<400> SEQUENCE: 5
gagtcagctg aaaattgtaa caaatcactt catacccc                              37

<210> SEQ ID NO 6
<211> LENGTH: 37
<212> TYPE: DNA
<213> ORGANISM: Artificial
<220> FEATURE:
<223> OTHER INFORMATION: Primer

<400> SEQUENCE: 6
gggtatgaag tgatttgtta caattttcag ctgactc                               37

<210> SEQ ID NO 7
<211> LENGTH: 32
<212> TYPE: DNA
<213> ORGANISM: Artificial
<220> FEATURE:
<223> OTHER INFORMATION: Primer

<400> SEQUENCE: 7
ggatgtttgc aaaaactata ctgaggcaaa gg                                    32

<210> SEQ ID NO 8
<211> LENGTH: 32
<212> TYPE: DNA
<213> ORGANISM: Artificial
<220> FEATURE:
<223> OTHER INFORMATION: Primer

<400> SEQUENCE: 8
cctttgcctc agtatagttt ttgcaaacat cc                                    32

<210> SEQ ID NO 9
<211> LENGTH: 30
<212> TYPE: DNA
<213> ORGANISM: Artificial
<220> FEATURE:
```

```
<223> OTHER INFORMATION: Primer

<400> SEQUENCE: 9
gctctggaag tcaatgaaac atacgttccc                                          30

<210> SEQ ID NO 10
<211> LENGTH: 30
<212> TYPE: DNA
<213> ORGANISM: Artificial
<220> FEATURE:
<223> OTHER INFORMATION: Primer

<400> SEQUENCE: 10
gggaacgtat gtttcattga cttccagagc                                          30

<210> SEQ ID NO 11
<211> LENGTH: 30
<212> TYPE: DNA
<213> ORGANISM: Artificial
<220> FEATURE:
<223> OTHER INFORMATION: Primer

<400> SEQUENCE: 11
gaaaatttcg acgccttggt gttgattgcc                                          30

<210> SEQ ID NO 12
<211> LENGTH: 27
<212> TYPE: DNA
<213> ORGANISM: Artificial
<220> FEATURE:
<223> OTHER INFORMATION: Primer

<400> SEQUENCE: 12
ggcggacctt gccgactata tctgtga                                             27

<210> SEQ ID NO 13
<211> LENGTH: 27
<212> TYPE: DNA
<213> ORGANISM: Artificial
<220> FEATURE:
<223> OTHER INFORMATION: Primer

<400> SEQUENCE: 13
ggtctcaaga aacctaggaa aagtggg                                             27
```